US 8,168,591 B2

(12) United States Patent
Takada et al.

(10) Patent No.: US 8,168,591 B2
(45) Date of Patent: May 1, 2012

(54) COMPOSITIONS AND METHODS RELATED TO ANTI-FGF AGENTS

(75) Inventors: Yoshikazu Takada, Davis, CA (US); Seiji Mori, Houston, TX (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/582,590

(22) Filed: Oct. 17, 2006

(65) Prior Publication Data
US 2007/0099834 A1 May 3, 2007

Related U.S. Application Data

(60) Provisional application No. 60/727,700, filed on Oct. 17, 2005.

(51) Int. Cl.
*A61K 38/18* (2006.01)
*C07K 14/50* (2006.01)
(52) U.S. Cl. ............... 514/9.1; 530/350; 530/399
(58) Field of Classification Search ............. None
See application file for complete search history.

(56) References Cited

U.S. PATENT DOCUMENTS

| 5,491,220 | A  | * | 2/1996 | Seddon et al. | 530/399 |
|---|---|---|---|---|---|
| 7,595,296 | B1 | * | 9/2009 | Blaber et al. | 514/12 |
| 7,659,379 | B1 | * | 2/2010 | Blaber et al. | 530/399 |
| 7,696,171 | B1 | * | 4/2010 | Blaber et al. | 514/12 |
| 7,776,825 | B1 | * | 8/2010 | Blaber et al. | 514/12 |
| 7,790,682 | B1 | * | 9/2010 | Blaber et al. | 435/320.1 |

OTHER PUBLICATIONS

Mori, S., et al,. "Direct Binding of Integrin αvβ3 to FGF1 Plays a Role in FGF1 Signalling," *The Journal of Biological Chemistry*, vol. 283(26), pp. 18066-18075 (Initial Publication: Apr. 25, 2008, Updated Publication: Jun. 27, 2008).

Rusnati, M., et al., "$\alpha_v\beta_3$ Integrin Mediates the Cell-adhesive Capacity and Biological activity of Basic Fibroblast Growth Factor (FGF-2) in Cultured Endothelial Cells," *Molecular Biology of the Cell*, vol. 8, pp. 2449-2461 (Dec. 1997).

* cited by examiner

*Primary Examiner* — Marianne P Allen
(74) *Attorney, Agent, or Firm* — Kilpatrick Townsend & Stockton LLP

(57) ABSTRACT

The invention relates to an isolated amino acid that can act as an antagonist to FGF signaling, comprising at least a portion of the FGF protein amino acid sequence, and including a mutation in either a) the integrin αvβ3 binding region of FGF-1; or b) the FGFR binding region of FGF-1.

9 Claims, 21 Drawing Sheets

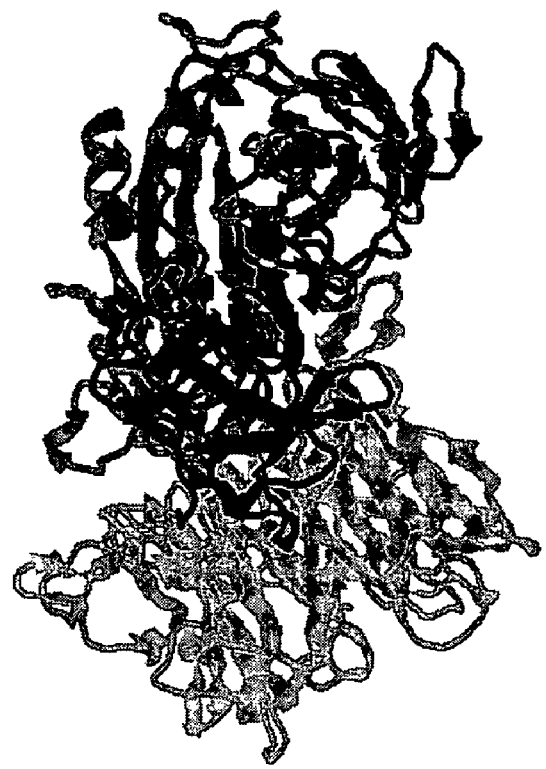
Fig. 2C

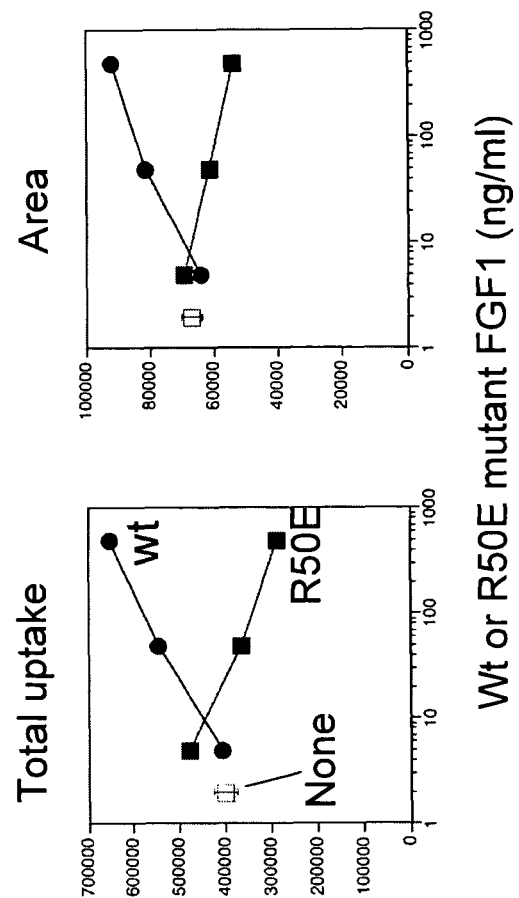
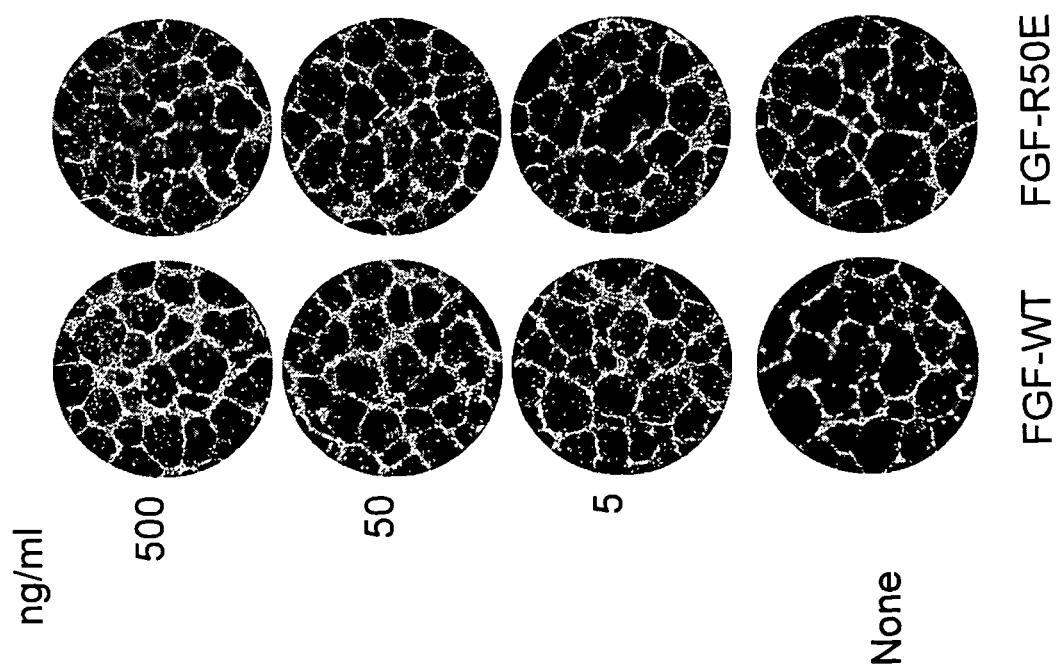
Fig. 9

Cells were serum-starved (1% FCS) for 48 h, and then treated with etoposide (100 μM) and FGF for 48 h.

```
                          SEQUENCE LISTING

<160> NUMBER OF SEQ ID NOS: 7

<210> SEQ ID NO 1
<211> LENGTH: 29
<212> TYPE: DNA
<213> ORGANISM: Homo sapiens

<400> SEQUENCE: 1
gcagatcttt taatctgcct ccagggaat                                29

<210> SEQ ID NO 2
<211> LENGTH: 29
<212> TYPE: DNA
<213> ORGANISM: Homo sapiens

<400> SEQUENCE: 2
gcgaattctt aatcagaaga gactggcag                                29

<210> SEQ ID NO 3
<211> LENGTH: 29
<212> TYPE: DNA
<213> ORGANISM: Homo sapiens

<400> SEQUENCE: 3
gcagatctcc cgccttgccc gaggatggc                                29

<210> SEQ ID NO 4
<211> LENGTH: 32
<212> TYPE: DNA
<213> ORGANISM: Homo sapiens

<400> SEQUENCE: 4
gcgaattctc agctcttagc agaagacatt gg                            32

<210> SEQ ID NO 5
<211> LENGTH: 30
<212> TYPE: DNA
<213> ORGANISM: Homo sapiens

<400> SEQUENCE: 5
gcggatccac agataacacc aaaccaaacc                               30
```

<210> SEQ ID NO 6
<211> LENGTH: 29
<212> TYPE: DNA
<213> ORGANISM: Homo sapiens

<400> SEQUENCE: 6
gcctcagtca cctctcttcc agggcttcc                                              29

<210> SEQ ID NO 7
<211> LENGTH: 155
<212> TYPE: PRT
<213> ORGANISM: Homo sapiens

<400> SEQUENCE: 7

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

COMPOSITIONS AND METHODS RELATED TO ANTI-FGF AGENTS

CONTINUING APPLICATION DATA

This application is a continuation in part of the United States Provisional Application No. 60/727,700, having a filing date of Oct. 17, 2005.

NOTICE

This invention was made with Government support under Grant No. GM47157, awarded by the National Institutes of Health. The Government has certain rights in this invention.

BACKGROUND OF THE INVENTION

1. Field of the Invention

The present invention relates to FGF-1 and mutants of FGF-1 affecting the signaling of cellular growth, differentiation, and angiogenesis.

2. References

Various publications are referred to in parentheses throughout this application. Each of these publications is incorporated by reference herein. Complete citations of scientific publications are set forth below, or in the text of the specification.

Assoian, R. K. (1997) Anchorage-dependent cell cycle progression. *J Cell Biol,* 136, 1-4.

Belford, D. A., Hendry, I. A. and Parish, C. R. (1992) Ability of different chemically modified heparins to potentiate the biological activity of heparin-binding growth factor 1: lack of correlation with growth factor binding. *Biochemistry,* 31, 6498-6503.

Brooks, P., Clark, R. and Cheresh, D. (1994a) Requirement of vascular integrin alpha v beta 3 for angiogenesis. *Science,* 264, 569-571.

Brooks, P., Montgomery, A., Rosenfeld, M., Reisfeld, R., Hu, T., Klier, G. and Cheresh, D. (1994b) Integrin alpha v beta 3 antagonists promote tumor regression by inducing apoptosis of angiogenic blood vessels. *Cell,* 79, 1157-1164.

Brooks, P. C., Stromblad, S., Klemke, R., Visscher, D., Sarkar, F. H. and Cheresh, D. A. (1995) Antiintegrin alpha v beta 3 blocks human breast cancer growth and angiogenesis in human skin. *J Clin Invest,* 96,.1815-1822.

Brown, K. J., Hendry, I. A. and Parish, C. R. (1995) Acidic and basic fibroblast growth factor bind with differing affinity to the same heparan sulfate proteoglycan on BALB/c 3T3 cells: implications for potentiation of growth factor action by heparin. *J Cell Biochem,* 58, 6-14.

Burgess, W. H., Shaheen, A. M., Ravera, M., Jaye, M., Donohue, P. J. and Winkles, J. A. (1990) Possible dissociation of the heparin-binding and mitogenic activities of heparin-binding (acidic fibroblast) growth factor-1 from its receptor-binding activities by site-directed mutagenesis of a single lysine residue. *J Cell Biol,* 111, 2129-2138.

Comoglio, P. M., Boccaccio, C. and Trusolino, L. (2003) Interactions between growth factor receptors and adhesion molecules: breaking the rules. *Curr Opin Cell Biol,* 15, 565-571.

DiGabriele, A. D., Lax, I., Chen, D. I., Svahn, C. M., Jaye, M., Schlessinger, J. and Hendrickson, W. A. (1998) Structure of a heparin-linked biologically active dimer of fibroblast growth factor. *Nature,* 393, 812-817.

Eliceiri, B. P. (2001) Integrin and growth factor receptor crosstalk. *Circ Res,* 89, 1104-1110.

Friedlander, M., Brooks, P. C., Shaffer, R. W., Kincaid, C. M., Varner, J. A. and Cheresh, D. A. (1995) Definition of two angiogenic pathways by distinct alpha v integrins. *Science,* 270, 1500-1502.

Friesel, R. E. and Maciag, T. (1995) Molecular mechanisms of angiogenesis: fibroblast growth factor signal transduction. *Faseb J,* 9, 919-925.

Frisch, S. M. and Screaton, R. A. (2001) Anoikis mechanisms. *Curr Opin Cell Biol,* 13, 555-562.

Fromm, J. R., Hileman, R. E., Weiler, J. M. and Linhardt, R. J. (1997) Interaction of fibroblast growth factor-1 and related peptides with heparan sulfate and its oligosaccharides. *Arch Biochem Biophys,* 346, 252-262.

Goodsell, D. S. and Olson, A. J. (1990) Automated docking of substrates to proteins by simulated annealing. *Proteins,* 8, 195-202.

Hynes, R. O. (2002) Integrins: bidirectional, allosteric signaling machines. *Cell,* 110, 673-687.

Kaplow, J. M., Bellot, F., Crumley, G., Dionne, C. A. and Jaye, M. (1990) Effect of heparin on the binding affinity of acidic FGF for the cloned human FGF receptors, flg and bek. *Biochem Biophys Res Commun,* 172, 107-112.

Klint, P. and Claesson-Welsh, L. (1999) Signal transduction by fibroblast growth factor receptors. *Front Biosci,* 4, D165-177.

Kwabi-Addo, B., Ozen, M. & Ittmann, M. The role of fibroblast growth factors and their receptors in prostate cancer. *Endocr Relat Cancer* 11, 709-24 (2004).

LaVallee, T. M., Prudovsky, I. A., McMahon, G. A., Hu, X. and Maciag, T. (1998) Activation of the MAP kinase pathway by FGF-1 correlates with cell proliferation induction while activation of the Src pathway correlates with migration. *J Cell Biol,* 141, 1647-1658.

Lishko, V. K., Kudryk, B., Yakubenko, V. P., Yee, V. C. and Ugarova, T. P. (2002) Regulated unmasking of the cryptic binding site for integrin alpha M beta 2 in the gamma C-domain of fibrinogen. *Biochemistry,* 41, 12942-12951.

Liu, J., Huang, C. and Zhan, X. (1999) Src is required for cell migration and shape changes induced by fibroblast growth factor 1. *Oncogene,* 18, 6700-6706.

Morris, G. M., Goodsell, D. S., Halliday, R. S., Fig Huey, R., Hart, W. E., Belew, R. K. and Olson, A. J. (1998) Automated docking using a Lamarckian genetic algorithm- and an empirical binding free energy function. *J Comp. Chem.,* 19, 1639-1662.

Morris, G. M., Goodsell, D. S., Huey, R. and Olson, A. J. (1996) Distributed automated docking of flexible ligands to proteins: parallel applications of AutoDock 2.4. *J Comput Aided Mol Des,* 10, 293-304.

Pages, G., Lenormand, P., L'Allemain, G., Chambard, J. C., Meloche, S. and Pouyssegur, J. (1993) Mitogen-activated protein kinases p42mapk and p44mapk are required for fibroblast proliferation. *Proc Natl Acad Sci U S A,* 90, 8319-8323.

Pellegrini, L., Burke, D. F., von Delft, F., Mulloy, B. and Blundell, T. L. (2000) Crystal structure of fibroblast growth factor receptor ectodomain bound to ligand and heparin. *Nature,* 407, 1029-1034.

Plotnikov, A. N., Hubbard, S. R., Schlessinger, J. and Mohammadi, M. (2000) Crystal structures of two FGF-FGFR complexes reveal the determinants of ligandreceptor specificity. *Cell,* 101, 413-424.

Powers, C. J., McLeskey, S. W. and Wellstein, A. (2000) Fibroblast growth factors, their receptors and signaling. *Endocr Relat Cancer,* 7, 165-197.

Prater, C. A., Plotkin, J., Jaye, D. and Frazier, W. A. (1991) The properdin-like type I repeats of human thrombospondin contain a cell attachment site. *J. Cell Biol.,* 112, 1031-1040.

Presta, M., Dell'Era, P., Mitola, S., Moroni, E., Ronca, R. and Rusnati, M. (2005) Fibroblast growth factor/fibroblast growth factor receptor system in angiogenesis. *Cytokine Growth Factor Rev,* 16, 159-178.

Rusnati, M., Tanghetti, E., Dell'Era, P., Gualandris, A. and Presta, M. (1997) alphavbeta3 integrin mediates the cell-adhesive capacity and biological activity of basic fibroblast growth factor (FGF-2) in cultured endothelial cells. *Molecular Biology of the Cell.,* 8, 2449-2461.

Sahni, A. and Francis, C. W. (2004) Stimulation of endothelial cell proliferation by FGF-2 in the presence of fibrinogen requires alphavbeta3. *Blood,* 104, 3635-3641.

Saphire, E. O., Parren, P. W., Pantophlet, R., Zwick, M. B., Morris, G. M., Rudd, P. M., Dwek, R. A., Stanfield, R. L., Burton, D. R. and Wilson, I. A. (2001) Crystal structure of a neutralizing human IGG against HIV-1: a template for vaccine design. Science, 293, 1155-1159.

Schlessinger, J. (2000) Cell signaling by receptor tyrosine kinases. *Cell,* 103, 211-225. Schwartz, M. A. and Assoian, R. K. (2001) Integrins and cell proliferation: regulation of cyclin-dependent kinases via cytoplasmic signaling pathways. *J Cell Sci,* 114, 2553-2560.

Schwartz, M. A. and Ginsberg, M. H. (2002) Networks and crosstalk: integrin signalling spreads. *Nat Cell Biol,* 4, E65-68.

Shimaoka, M. and Springer, T. A. (2003) Therapeutic antagonists and conformational regulation of integrin function. *Nat Rev Drug Discov,* 2, 703-716.

Takagi, J., Erickson, H. P. and Springer, T. A. (2001) C-terminal opening mimics 'inside-out' activation of integrin alpha5beta1. *Nat Struct Biol,* 8, 412-416.

Tanghetti, E., Ria, R., Dell'Era, P., Urbinati, C., Rusnati, M., Ennas, M. G. and Presta, M. (2002) Biological activity of substrate-bound basic fibroblast growth factor (FGF2): recruitment of FGF receptor-1 in endothelial cell adhesion contacts. *Oncogene,* 21, 3889-3897.

Thornton, S. C., Mueller, S. N. and Levine, E. M. (1983) Human endothelial cells: use of heparin in cloning and long-term serial cultivation. *Science,* 222, 623-625.

Ullrich, A. and Schlessinger, J. (1990) Signal transduction by receptors with tyrosine kinase activity. Cell, 61, 203-212.

Wang, W. and Malcolm, B. A. (1999) Two-Stage PCR Protocol Allowing Introduction of Multiple Mutations, Deletions and Insertions Using QuikChange ™ Site-Directed Mutagenesis. *BioTechniques,* 26, 680-682.

Yokoyama, K., Erickson, H. P., Ikeda, Y. and Takada, Y. (2000) Identification of amino acid sequences in fibrinogen y-chain and tenascin C C-terminal domains critical for binding to integrin $\alpha v \beta 3$. *J. Biol. Chem.,* 275, 16891-16898.

Yokoyama, K., Zhang, X. P., Medved, L. and Takada, Y. (1999) Specific binding of integrin $\alpha V \beta 3$ to the fibrinogen $\gamma$ and $\alpha E$ chain C-terminal domains. *Biochemistry,* 38, 5872-5877.

Zhu, H., Anchin, J., Ramnarayan, K., Zheng, J., Kawai, T., Mong, S. and Wolff, M. E. (1997) Analysis of high-affinity binding determinants in the receptor binding epitope of basic fibroblast growth factor. Protein Eng, 10, 417-421.

3. Description of Related Art

Fibroblast growth factors (FGFs) constitute a family of heparin-binding polypeptides involved in the regulation of biological responses such as growth, differentiation, and angiogenesis. They are also implicated in inflammation, excess wound healing, and resistance of tumor cells to chemotherapeutic agents (chemoresistance).

The FGF family currently consists of 24 members, with FGF-1 (acidic FGF) and FGF-2 (basic FGF) the most extensively studied. The biological effects of FGFs are mediated by four structurally related receptor tyrosine kinases, denoted FGFR1, FGFR2, FGFR3, and FGFR4. The binding of FGF to its receptor results in receptor dimerization and subsequent autophosphorylation on specific tyrosine residues within the intracellular domain (Klint and Claesson-Welsh, 1999; Powers et al., 2000; Presta et al., 2005; Ullrich and-Schlessinger, 1990)

Integrins are a family of cell adhesion receptors that recognize extracellular matrix ligands and cell surface ligands (Hynes, 2002). Integrins are transmembrane $\alpha$-$\beta$ heterodimers, and at least 18 $\alpha$ and $\beta$ subunits are known (Shimaoka and Springer, 2003). Integrins transduce signals to the cell upon ligand binding, and their functions are in turn regulated by the signals from within the cell (Hynes, 2002). Ligation of integrins triggers a large variety of signal transduction events that serve to modulate cell behavior including proliferation, survival/apoptosis, shape, polarity, motility, gene expression, and differentiation. Integrin-stimulated pathways are very similar to those triggered by growth factor receptors and are intimately coupled with them. It has been proposed that many cellular responses to soluble growth factors, such as epidermal growth factor, platelet-derived growth factor, and thrombin, are dependent upon the cell's adherence to extracellular matrix ligands via integrins. Integrins lie at the basis of such anchorage-dependent cell survival and proliferation (Assoian, 1997; Frisch and Screaton, 2001; Schwartz and Assoian, 2001).

It has been proposed that FGF-2-induced angiogenesis requires integrin signaling from the extracellular matrix (crosstalk between integrins and FGF receptors). Indeed antibody against integrin $\alpha v \beta 3$ blocks FGF-2-induced angiogenesis (Brooks et al., 1994a; Brooks et al., 1994b). It has been reported that FGF-2 enhances $\alpha v \beta 3$ expression during angiogenesis (Brooks et al., 1994a). Antibody or cyclic peptide antagonist of $\alpha v \beta 3$ inhibits this $\alpha v \beta 3$ upregulation (Brooks et al., 1994a; Brooks et al., 1995; Friedlander et al., 1995). It has been shown that integrin and growth factors are colocalized under certain condition. For example coimmunoprecipitation studies revealed direct biochemical interaction between $\alpha v \beta 3$ and FGFR1 in the presence of both FGF-2 and fibrinogen (Sahni and Francis, 2004). These findings suggest integrin and FGFR are colocalized on the membrane in the presence of FGF-2. It has not been established how integrins and FGFR crosstalk in FGF-2 signaling.

It has been reported that substrate-bound FGF-2 promotes endothelial cell adhesion by interacting with integrin $\alpha v \beta 3$ (Rusnati et al., 1997) and induces endothelial cell proliferation, motility, and the recruitment of FGFR1 in cell substrate contact (Tanghetti et al., 2002). Anti-$\alpha v \beta 3$ antibodies block cell proliferation on immobilized FGF-2, but deletion of the tyrosine kinase portion of FGFR blocks cell proliferation induced by inmmobilized FGF-2. Thus it has been proposed that $\alpha v \beta 3$ is required but not sufficient to transduce mitogenic signals of FGF-2 (Tanghetti et al., 2002). It is unclear how integrins interact with FGF-2 or whether this interaction is biologically relevant since heat-denatured FGF-2 still supports integrin binding (Tanghetti et al., 2002).

SUMMARY OF INVENTION

The invention relates to an isolated amino acid comprising at least a portion of the FGF protein amino acid sequence, and including a mutation in the integrin $\alpha v \beta 3$ binding region of FGF-1.

In one preferred embodiment, the isolated amino acid comprises a mutation in the region Asn-33, Gly-34, Gly-35. In another preferred embodiment, the isolated amino acid comprises a mutation in the region His-36, Arg-39, Leu-41. In a further preferred embodiment the isolated amino acid comprises a mutation in the region Asp-43, Thr-45, Val-46. In a different preferred embodiment, the isolated amino acid comprises a mutation in the region Asp-47, Gly-48, Thr-49.

In a further preferred aspect of this embodiment, the isolated amino acid comprises a mutation in the region Arg-50, Asp-51, Arg-52. In a further preferred aspect of this embodiment, the isolated amino acid comprises a glutamine substitution for Arg-50. In a still further preferred aspect, the isolated amino acid is the protein R50E.

In a further preferred embodiment, the isolated amino acid comprises a mutation in the region Ser-53, Asp-54.

In a different preferred embodiment, the isolated amino acid comprises a mutation in the region Lys-127, Lys-128, Asn-129. In a further preferred aspect of this embodiment, the isolated amino acid comprises a glutamine substitution for Lys-127 and Lys-128. In a still further preferred aspect, the isolated amino acid is the mutant 4×E.

In a different preferred embodiment, the isolated amino acid comprises a mutation in the region Gly-130, Ser-131, Cys-132. In a different preferred embodiment, the isolated amino acid comprises a mutation in the region Lys-133, Arg-134, Arg-137. In a further preferred aspect of this embodiment, the isolated amino acid comprises a glutamine substitution for Lys-133 and Arg-134. In a still further preferred aspect, the isolated amino acid is the mutant 4×E.

In a different preferred embodiment, the isolated amino acid comprises a mutation in the region 138, Gly-141, Gln-142.

In a different preferred embodiment, the isolated amino acid binds to FGFR, and preferably acts as a dominant negative mutant against FGF inducing activity.

In another aspect of the invention, the isolated amino acid comprises a mutation in the region where the amino acid blocks the angiogenesis inducing activity of FGF-1. In a further aspect of this preferred embodiment, the isolated amino acid blocks the tumor growth inducing activity of FGF. In a different aspect of the invention, the isolated amino acid blocks the inflammation inducing activity of FGF. In still different aspect of the invention, the isolated amino acid blocks the excess wound healing inducing activity of FGF. In a further aspect of the invention, the isolated amino acid blocks the resistance of tumor cells to chemotherapeutic agents.

The isolated amino acid preferably acts as an antagonist to FGF signaling.

In a different embodiment, the isolated amino acid comprises at least a portion of the FGF protein amino acid sequence, and includes a mutation in the FGFR binding region of FGF-1. The isolated amino acid preferably binds to integrin αvβ3. In one preferred embodiment, the isolated amino acid comprises a mutation in the region of amino acids 100 to 110 of FGF-1. In a further such embodiment, the isolated amino acid is the mutant 3×A. The isolated amino acid preferably acts as a dominant negative mutant against FGF inducing activity.

The invention further comprises a pharmaceutical composition containing the amino acid. The pharmaceutical composition preferably is selected from the group of pharmaceutical compositions consisting of a diagnostic agent, a preventive agent, and a therapeutic agent for disease condition involving accelerated or abnormal cell growth.

In a different aspect of the embodiment, the accelerated or abnormal cell growth is selected from the group of conditions consisting of angiogenesis, cancer growth, inflammation and excess wound healing.

In a further aspect of the embodiment, the cancer growth condition is selected from the group of conditions consisting of acute myelogenous leukemia, breast cancer, prostate cancer, colon cancer, hepatic cancer, myeloma, uterine leiomyoma, malignant tumor, or solid tumor.

In a still different aspect of the embodiment, the inflammation condition is selected from the group of conditions consisting of rheumatoid arthritis (RA), lupus (SLE), inflammatory bowel diseases (IBD), experimental allergic encephalomyelitis (EAE), multiple sclerosis (MS), and diabetic retinopathy.

In another aspect of the embodiment, the angiogenesis condition is selected from the group of conditions consisting of cancer, diabetic blindness, age-related macular degeneration, rheumatoid arthritis and psoriasis.

In one preferred embodiment, the pharmaceutical composition will further comprise a carrier.

The invention also provides a method of reducing FGF signaling activity in a mammal, the method comprising dosing the mammal with an effective amount of the pharmaceutical composition. In one preferred aspect of the invention, the pharmaceutical composition is administered to the mammal orally. In another preferred embodiment, the mammal is a human.

In a different preferred aspect of the invention, the pharmaceutical composition is administered to the mammal topically. In a still different preferred aspect of the invention, the pharmaceutical composition is administered to the mammal intravenously.

The method preferably involves a mammal that has, or is at risk for developing, a vascularized solid tumor or metastases from a primary tumor.

In a further preferred embodiment, the method comprises the step of administering to the mammal another compound that inhibits tumor angiogenesis. In a preferred such aspect of the invention, the additional compound is chosen from a group comprising CV 3988, WEB 2086, INF-2.alpha., TNP-470, endostatin, SU 5416, SU 6668, batimistat, angiostatin; and celecoxib.

A. Recombinant Soluble αvβ3 Bound to Immobilized FGF-1 and FGF-2.

Wells of 96-well microtiter plates were coated with 10 μg/ml FGF-1 or FGF-2 and remaining protein binding sites were blocked with 1 mg/ml BSA. Recombinant soluble αvβ3 (50 μg/well at 5 μg/ml in Hepes-Tyrode buffer supplemented with 1 mM $MnCl_2$) was added to wells and incubated for 1 h at room temperature. Soluble αvβ3 was incubated with 10 μg/ml 7E3 (white bar) or mouse IgG (black bar) for 10 min on ice prior to adding to the wells. BSA (circle) was used as a negative control. Data is shown as means +/−SD of triplicate experiments.

B. Competition of FGF-1 with γC for Binding to Soluble αvβ3.

FGF-1 (10 μg/m) was immobilized to the plastic plate. Soluble αvβ3 was added to the wells together with increasing concentrations of soluble γC. Binding was determined as described in A. Data is shown as percent binding +/−SD of triplicate experiments with no addition of γC as 100.

C. FGF-1 Supported Adhesion of αvβ3-K562 Cells that Express Integrins αvβ3 and α5β1.

Wells of 96-well microtiter plates were coated with FGF-1 at the indicated concentrations and remaining protein binding sites were blocked with 1 mg/ml BSA. Hepes-Tyrode buffer supplemental with 1 mM $MnCl_2$) was used for adhesion assays. Prior to incubation with immobilized FGF-1, αvβ3-K562 cells were treated with 10 µg/ml anti-β3 function-blocking antibody 7E3 (triangle), anti-α5 function-blocking antibody KH72 (square), both 7E3 and KH72 (circle), or mouse IgG (diamond). BSA (cross) was used as a negative control. Data is shown as means +/-SD of triplicate experiments.

D. FGF-1 Supported Adhesion of Mock-transfected K562 Cells that Express α5β1.

K562 cells were treated with 10 µg/ml anti-α5 function-blocking antibody KH72 (square) or mouse IgG (diamond) for 10 min on ice. Hepes-Tyrode buffer supplemented with 1 mM $MnCl_2$) was used for adhesion assays. Bound cells were quantified by measuring endogenous phosphatase activity. BSA (cross) was used as a negative control. Data is shown as means +/-SD of triplicate experiments.

Figure 2A:
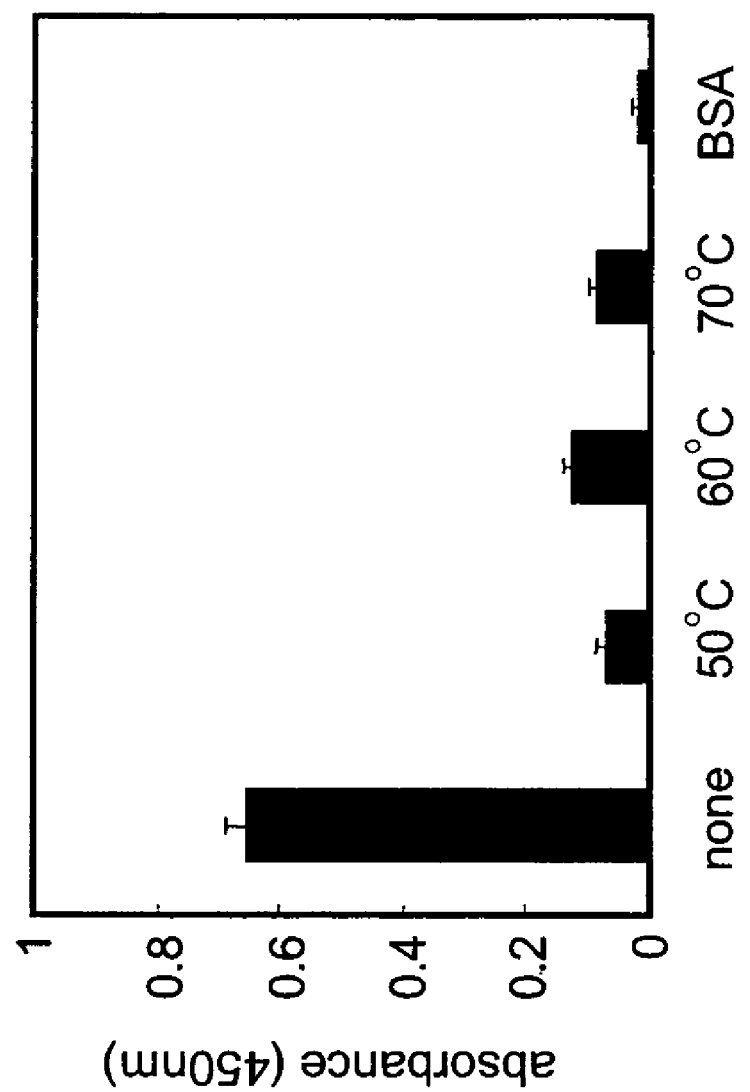
Figure 2B:
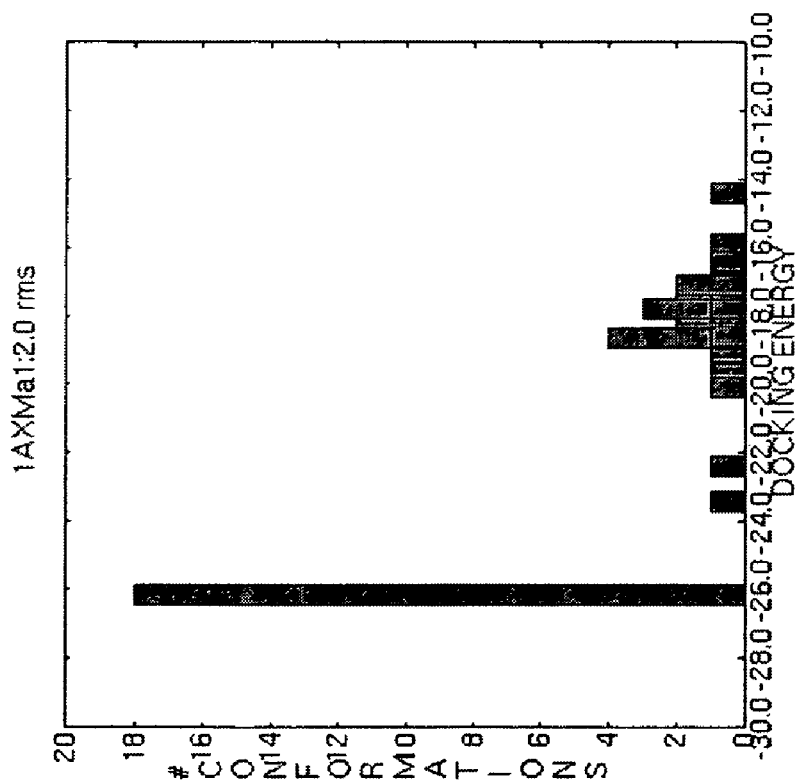
Figure 2D:
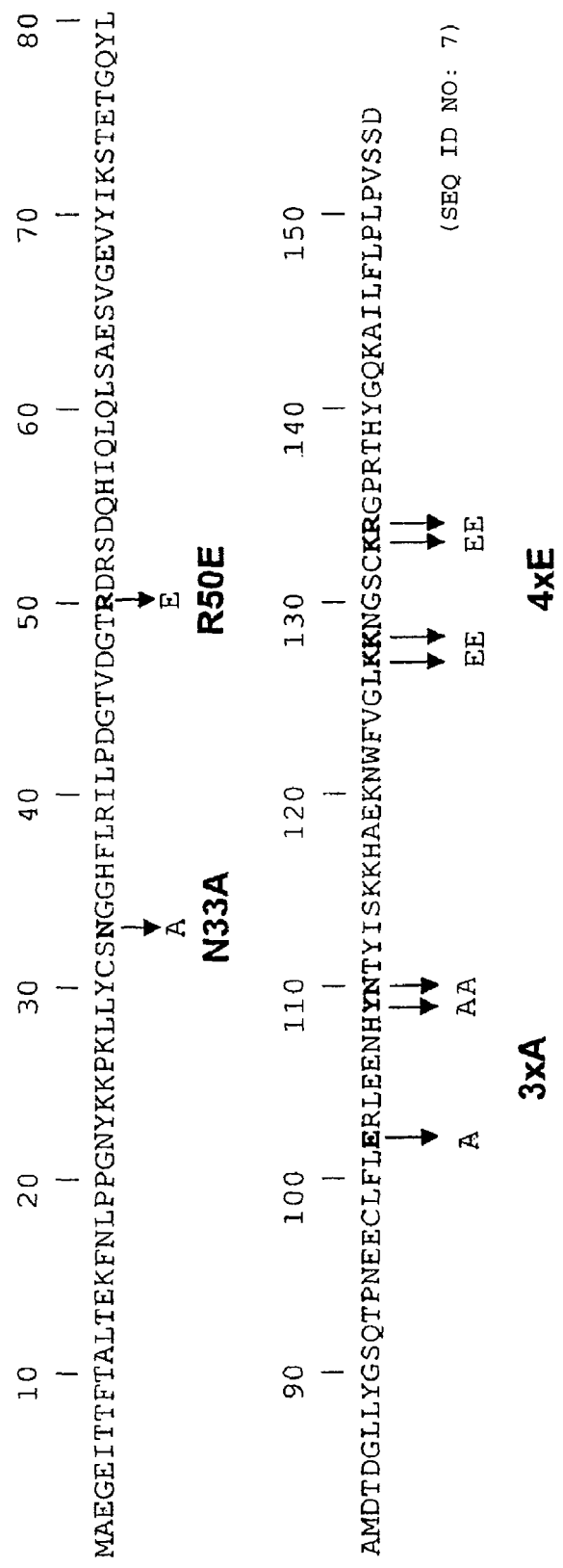
Figure 3A:
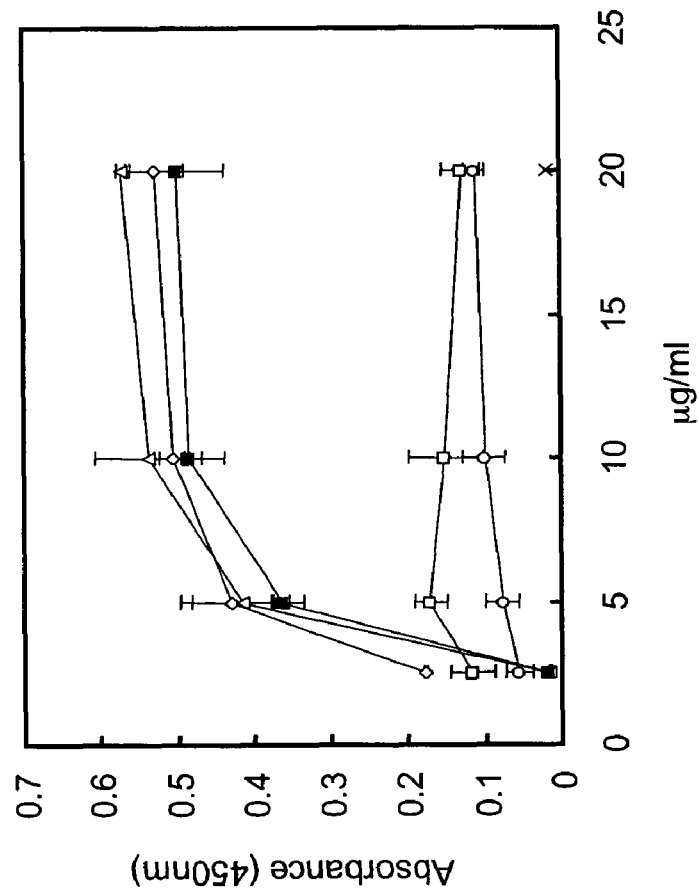
Figure 3B:
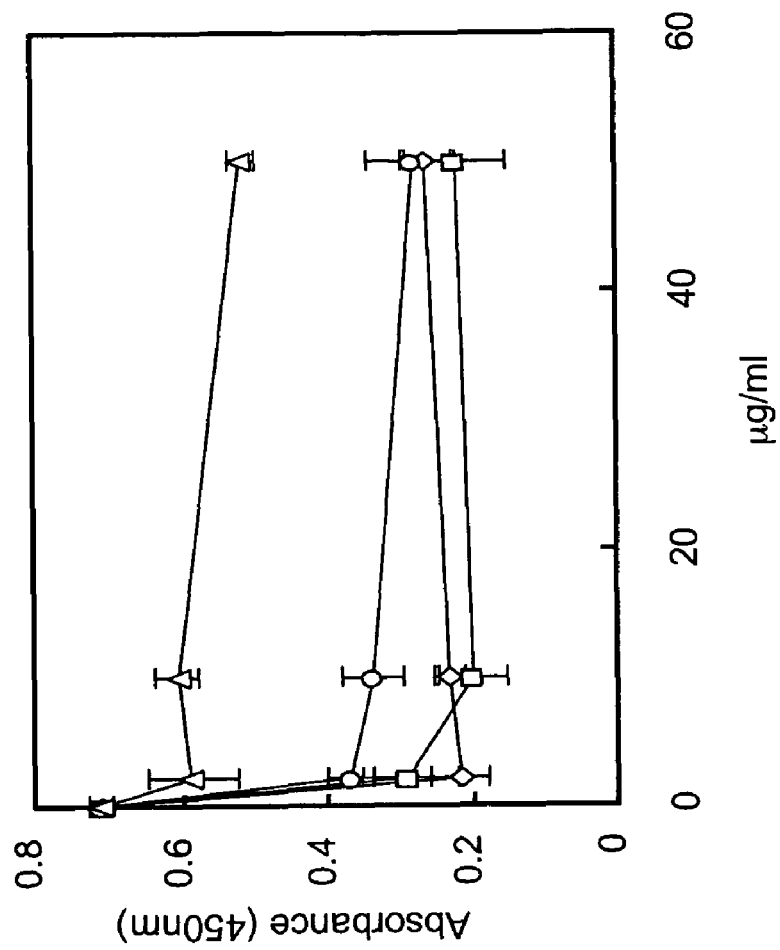
Figure 3C:
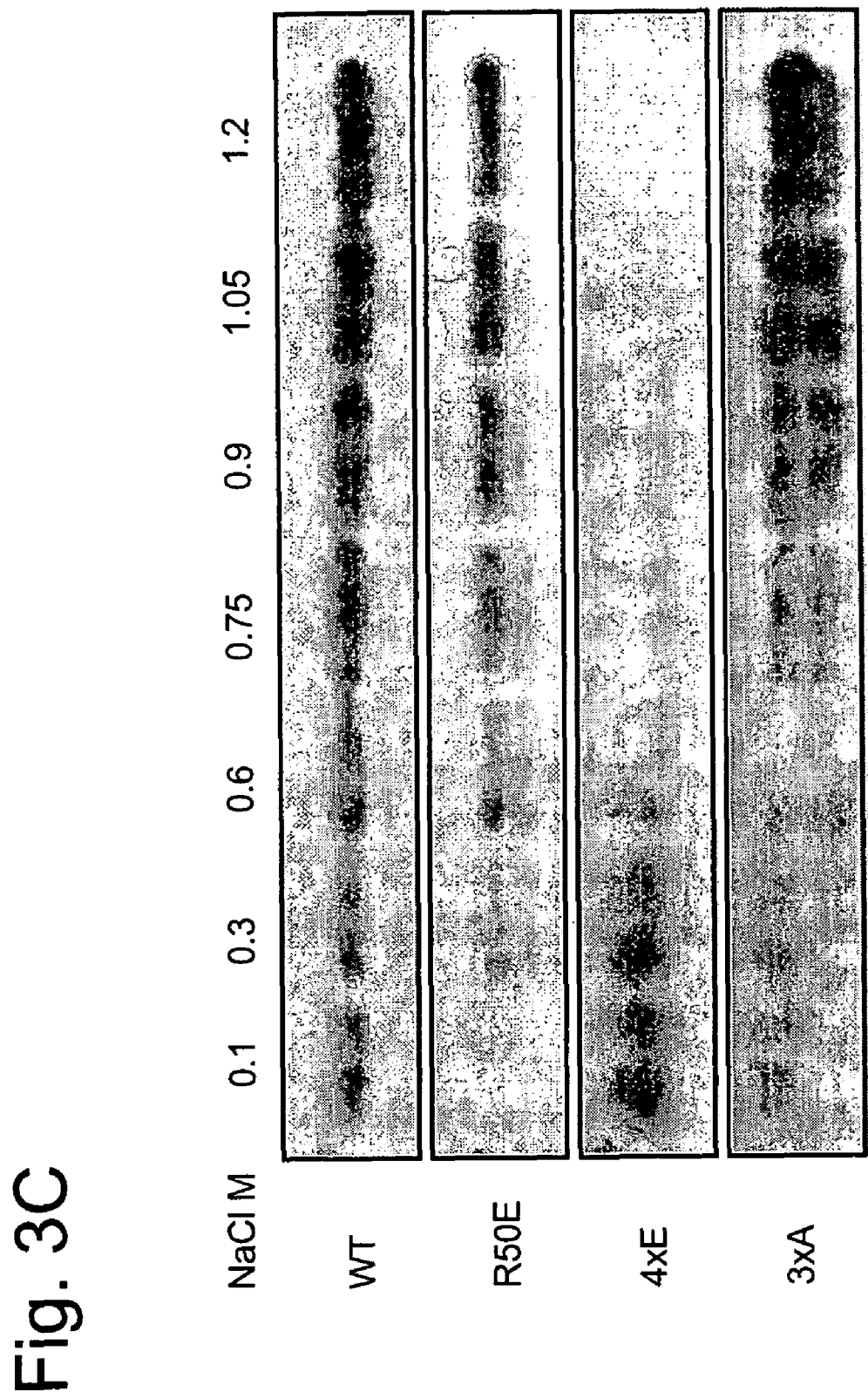
Figure 3D:
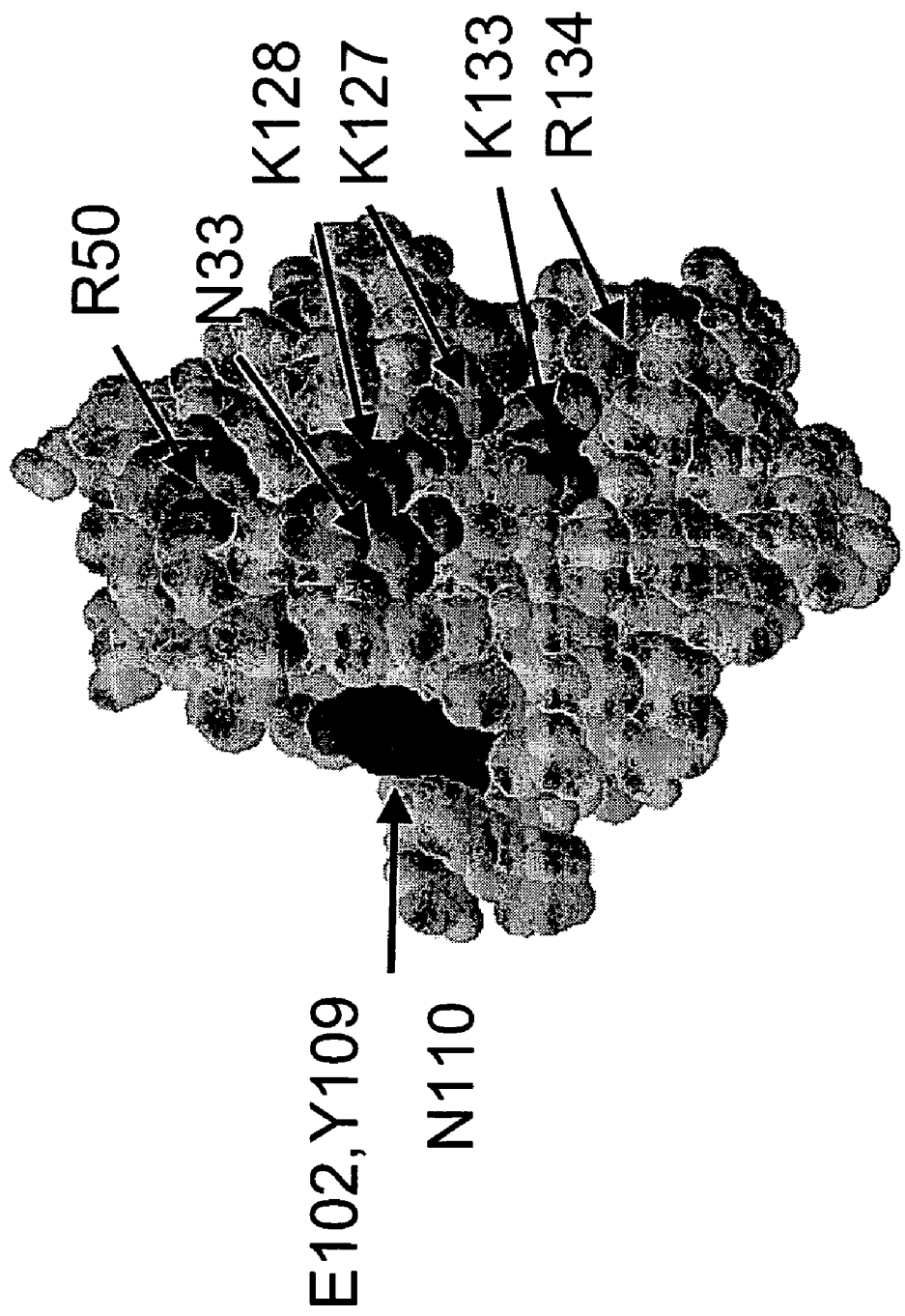

FIG. 2. Docking Simulation of FGF-1-αvβ3 Interaction.

A. Effect of Heat Denaturation on αvβ3 Binding.

FGF-1 (10 µg/m) was heat-treated at indicated temperature for 10 min prior to immobilization. Binding of soluble αvβ3 was determined as described in FIG. 1. Data is shown as percent binding +/-SD of triplicate experiments.

B and C. Docking Simulation of FGF-1-integrin Interaction.

Docking simulation of interaction between FGF-1 (PDB code 1AXM) and integrin αvβ3 (PDB code 1L5G) was performed as described in the Method section using AutoDock3. Histogram of the docked conformations (2 angstrom RMSD) (B) shows that they are nicely clustered with the lowest docking energy −26.3 Kcal/mol (cluster 1). The simulation predicts that the conformations in cluster 1 (shown in C) represent the most stable conformation of FGF-1 when FGF-1 interacts with integrin αvβ3.

D. Mutations Made to FGF-1.

As described herein and shown in the figure, various mutations were made to FGF-1.

FIG. 3. Effect of FGF-1 Mutations on FGF-1 Signaling.

A. The R50E Mutation of FGF-1 Blocked the Binding to Integrin αvβ3.

Amino acid residues in the integrin-binding site or in the FGFR-binding site were mutated individually or in groups. Wild-type (diamond), R50E (open square), N33A (closed square), 4×E (circle), 3×A (triangle) were coated to a plastic plate various concentration as indicated and the binding of soluble αvβ3 was determined as described in FIG. 2. BSA (cross) was used as a negative control. The results show that mutations in the predicted integrin-binding site blocked αvβ3 binding, but that those in the FGFR-binding site did not. "4×E" represents the K127E/K128E/K133E/R134E mutant. "3×A" represents the E1 02A/Y109A/Q110A mutant.

B. The 3×A Mutation of FGF-1 Effectively Blocked the Binding of the FGFR1 but the 4×E or R50E Mutation Did Not.

One µg/mi biotinylated FGF-1 and increasing concentrations of unlabelled FGF-1 or FGF-1 mutants were incubated for 1 h at RT with immobilized FGF receptor D2D3 fragments. Then the plate was washed and the bound biotinylated FGF were measured using an avidin conjugated HRP. Unlabeled wild-type (diamond) FGF-1, the R50E (square), 4×E (circle), and 3×A (triangle) FGF-1 mutants were used.

C. The 4×E Mutation of FGF-1 Completely Blocked Heparin Binding but the R50E or 3×A Mutation Did Not.

Partially purified wt and mutant FGF1 in 100 mM NaCl and 50 mM Tris (pH 7.4) were applied to a heparin sepharose column (1 ml bed volume). The column was washed with the same buffer and bound proteins were eluted with a stepwise increase in NaCl concentration from 0.1 to 1.2 M. Fractions were analyzed by SDS-polyacrylamide gradient gel electrophoresis. Proteins were visualized by Coomassie Brilliant Blue staining.

D. Positions of the Amino Acid Residues Critical for Integrin Binding (Red),Both Heparin 1R and Integrin Binding (Purple) and FGFR Binding (Blue).

Figure 4:
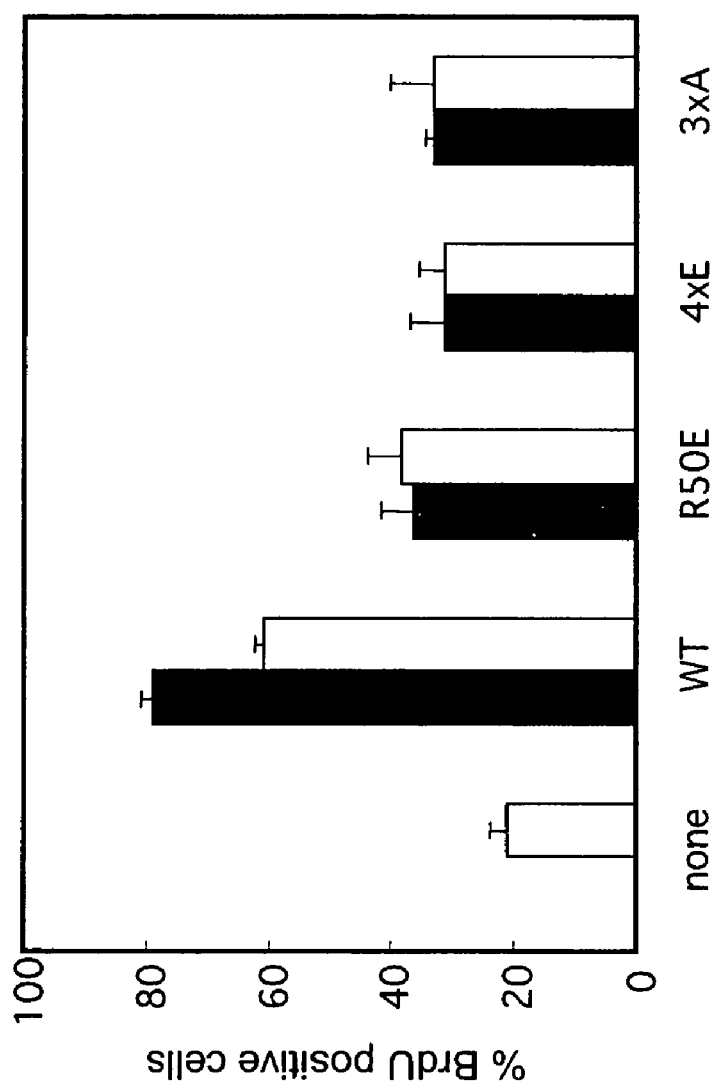

FIG. 4. FGF-1 Mutations that Block Integrin Binding Blocked FGF-1 Induced DNA Synthesis.

Balb 3T3 cells were plated on cover slips in 6-well culture plates, serum starved (DMEM, 0.4% fetal calf serum) for 48 h, and stimulated with 5 ng/ml wild-type and mutant FGF-1s in the presence of 5 µg/ml heparin for 24 h. BrdU was added to the medium for the last 6 h of the incubation. Cells were fixed and incubated with anti BrdU antibody. BrdU incorporated cells were stained with DAB. The mean value of BrdU positive cells from wild type-treated culture was set to 100%, and the corresponding results from mutant-treated cultures were scaled accordingly. Results are shown as means±S.D. Asterisks indicate significant differences ($p<0.05$) compared with wild type treatment.

Figure 5:
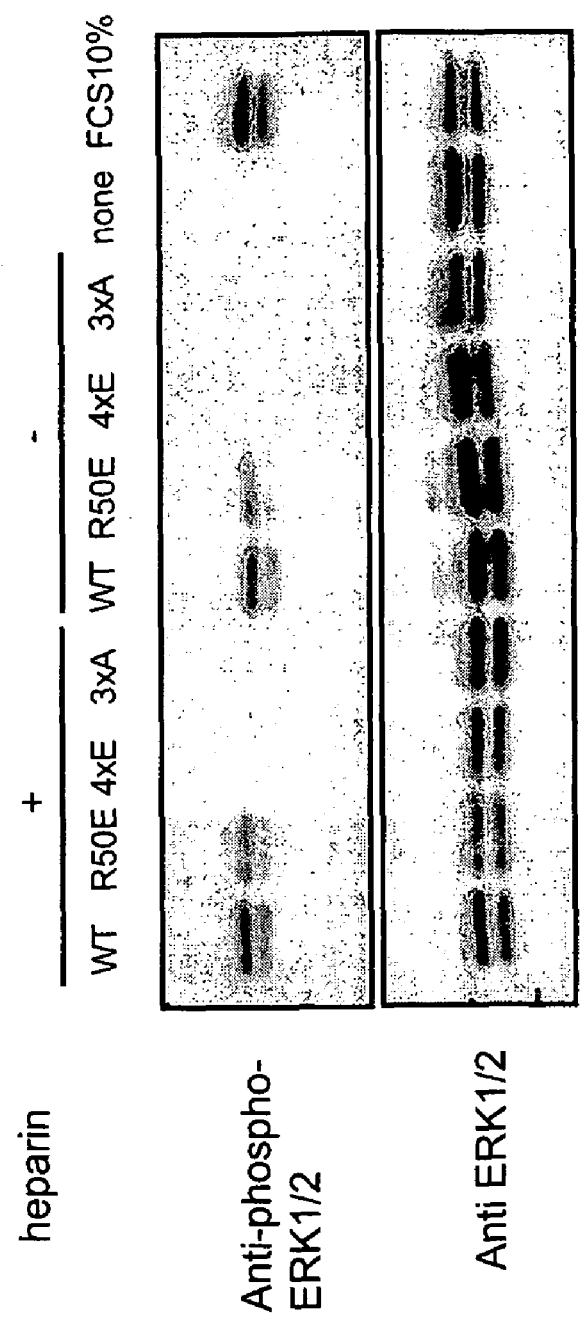

FIG. 5. FGF-1 Mutations that Block Integrin Binding Blocked FGF-1 Induced ERK1/2 Activation.

Serum starved Balb3T3 cells were stimulated with wild-type and mutant FGF-1s (5 ng/ml) in the presence or absence of 5 µg/ml heparin for 10 min at 37° C. Cell lysates were analyzed by western blotting with anti-phospho ERK1/2 (anti phospho-ERK). Total amount of ERK1/2 in each lane was determined by blotting with anti-ERK1/2. Controls contain medium alone (none) or medium containing 10% fetal calf serum (FCS).

Figure 6A:
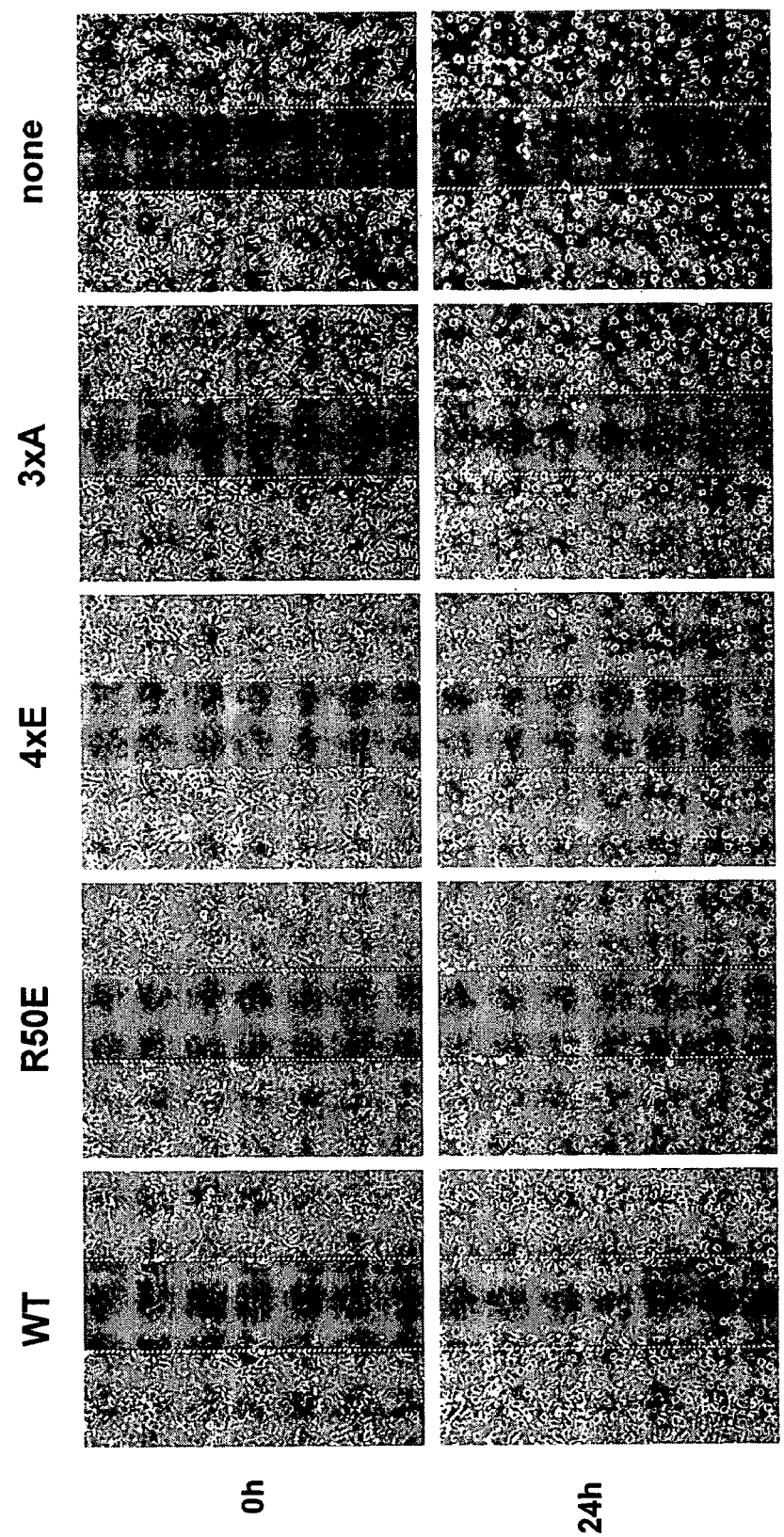
Figure 6B:
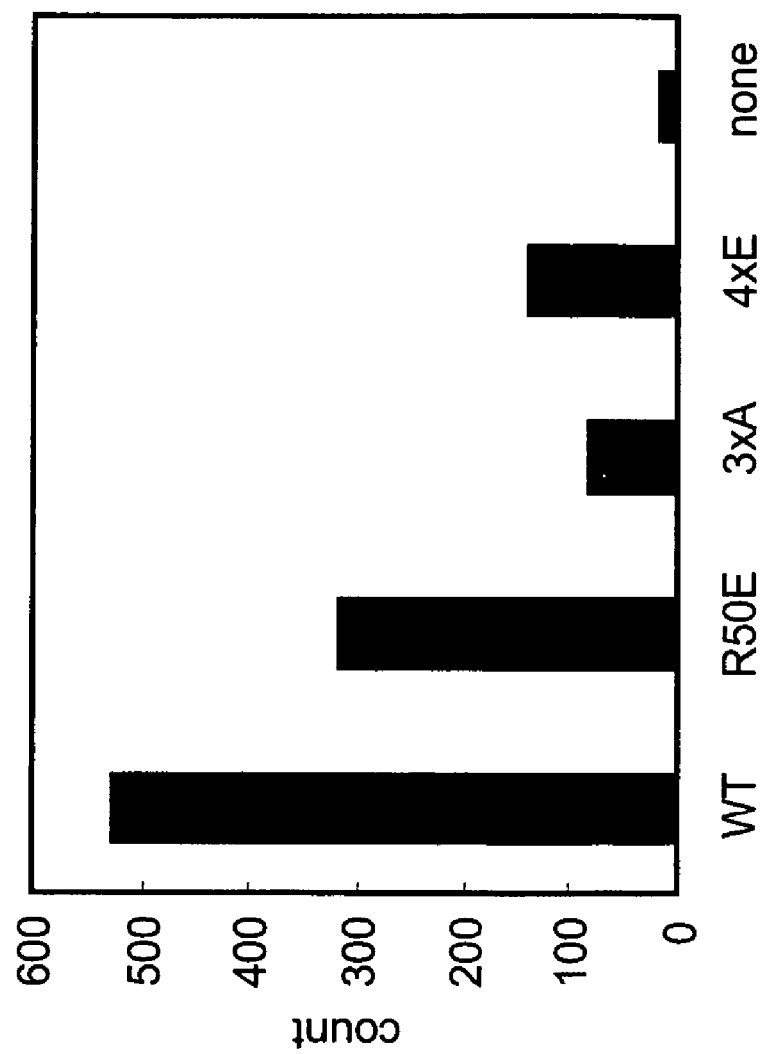

FIG. 6. FGF-1 Mutations that Block Integrin Binding Blocked FGF-1 Induced Migration of Balb 3T3 cell.

A. Scratch Wound Healing Assays.

Confluent serum-starved Balb 3T3 cells were scratched. After washing with serum-free medium, cells were incubated in DMEM containing 5 µg/ml heparin and 5 ng/ml wild-type or mutant FGF-1s for 24 h at 37° C. Controls contain medium alone (none) or medium containing 10% fetal calf serum (FCS).

B. Chemotaxis Assays.

The bottom of the polycarbonate filter of the Transwell apparatus was coated with 10 µg/ml of fibronectin. The lower chamber contained 600 µl of serum-free DMEM containing 5 ng/ml wild-type or mutants FGF-1. Balb 3T3 cells ($10^5$ cells/filter) were plated on filter and incubated 37° C. for 24 h, and cells were stained with crystal violet. Cells that migrated to the bottom side of the membrane were counted. Results are expressed as means of the number of migrated cells in 2 fields.

Figure 7:
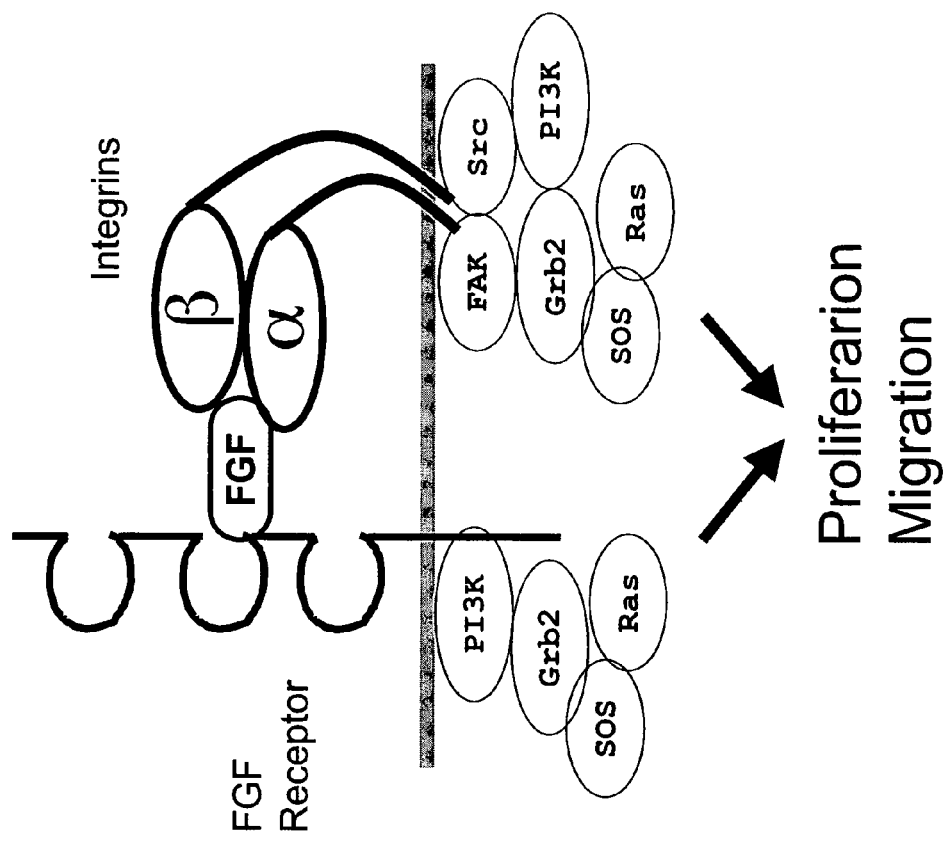

FIG. 7. A Potential Role of Integrin-FGF Interaction in FGF Signaling.

The present study establishes that FGF mutations that block integrin binding blocked FGF1-induced cell proliferation, MAP kinase activation, cell migration and chemotaxis. This shows that direct binding of integrins to FGF is required for FGF signaling. Heparin did not reverse the inhibitory effects of the R5OE mutation in FGF-1 signaling, suggesting that integrins and heparin play distinct roles in FGF signaling. Mutations that block integrin binding did not block FGFR binding and vise versa, showing that integrins and FGFR can simultaneously interact with FGF on the cell surface, though the formation of ternary complex could not be shown in this study. In this model integrins bind to FGF instead of extracellular matrix ligands.

Also shown is that integrins and FGFR are co-localized in the focal contacts, and many signaling molecules in the growth factor and integrin signaling pathways are recruited. Integrin antagonists can block the FGF-integrin crosstalk and thereby FGF signaling as in the current model. This may be one mechanism of the integrin FGF crosstalk.

Figure 8:
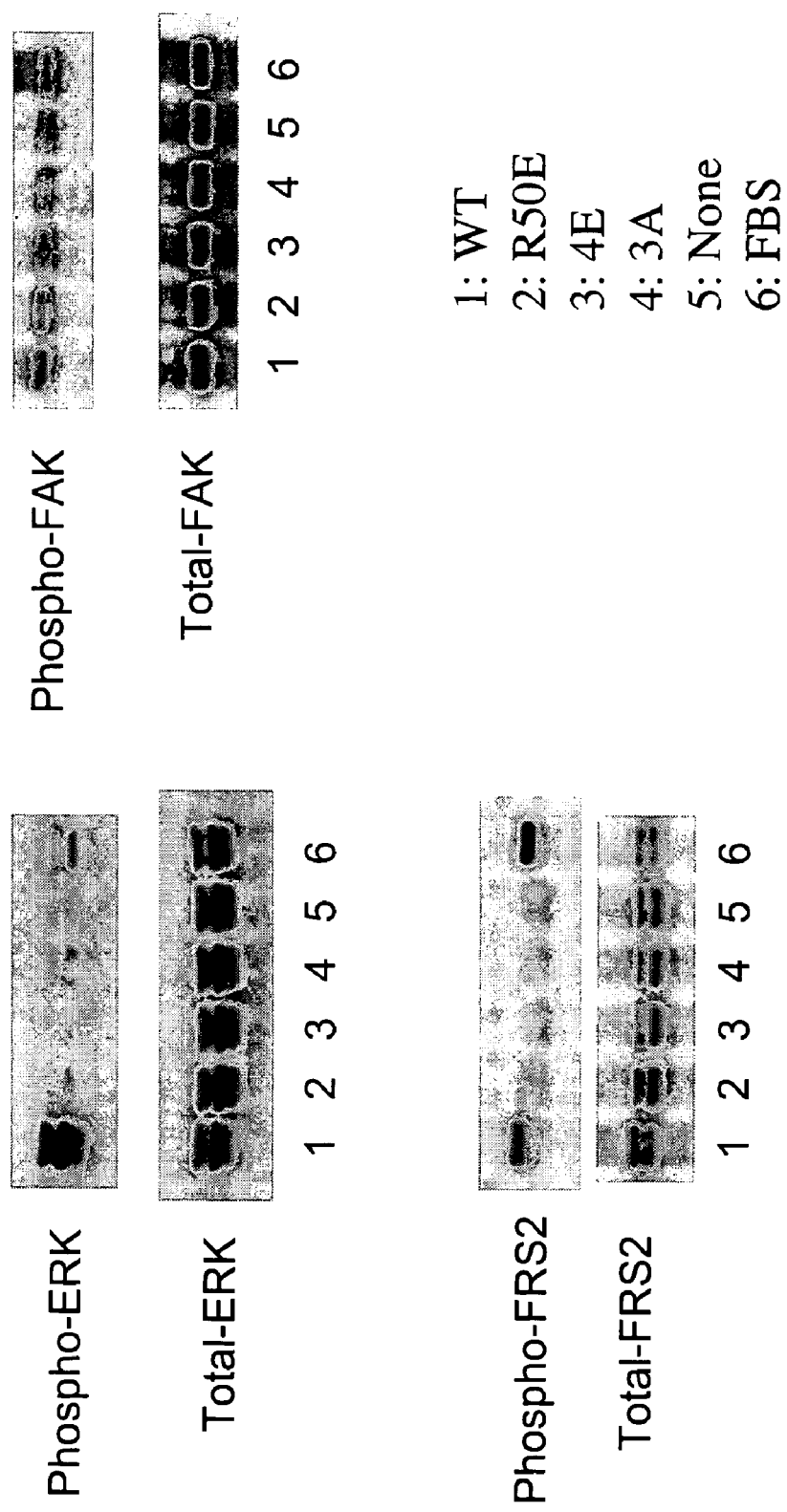

FIG. 8. FRS2 Phosphorylation.

FIG. 8 shows the effect of mutations of FGF1 on phosphorylation of MAP kinase, focal adhesion kinase (FAK), and FGF receptor substrate-2 (FRS2$\alpha$) in mouse fibroblasts. The same cell lysates as described above were analyzed by western blotting with anti-phospho FRS2 or anti-FRS2, where; 1: Wild type; 2: R50E; 3:4×E; 4:3×A; 5: None; and 6: FBS.

FIG. 9. Tube Formation by Endothelial Cells.

FIG. 9 demonstrates the suppression of tube formation by HMVEC on Matrigel by the integrin-binding-defective FGF1 mutants. Digital images were taken by using a fluorescent microscope and analyzed by using ImageJ, using human microvascular endothelial (HMVE) cells added to the matrix-coated wells of 96-well plates at 2×10⁴ cells/well in medium M-131 plus 0.1% hydrocortisone and 0.1% FBS for. Cells were incubated for 24 h in the presence of wt or mutant FGF. To enhance images, calcein AM was added to the medium.

Figure 10:
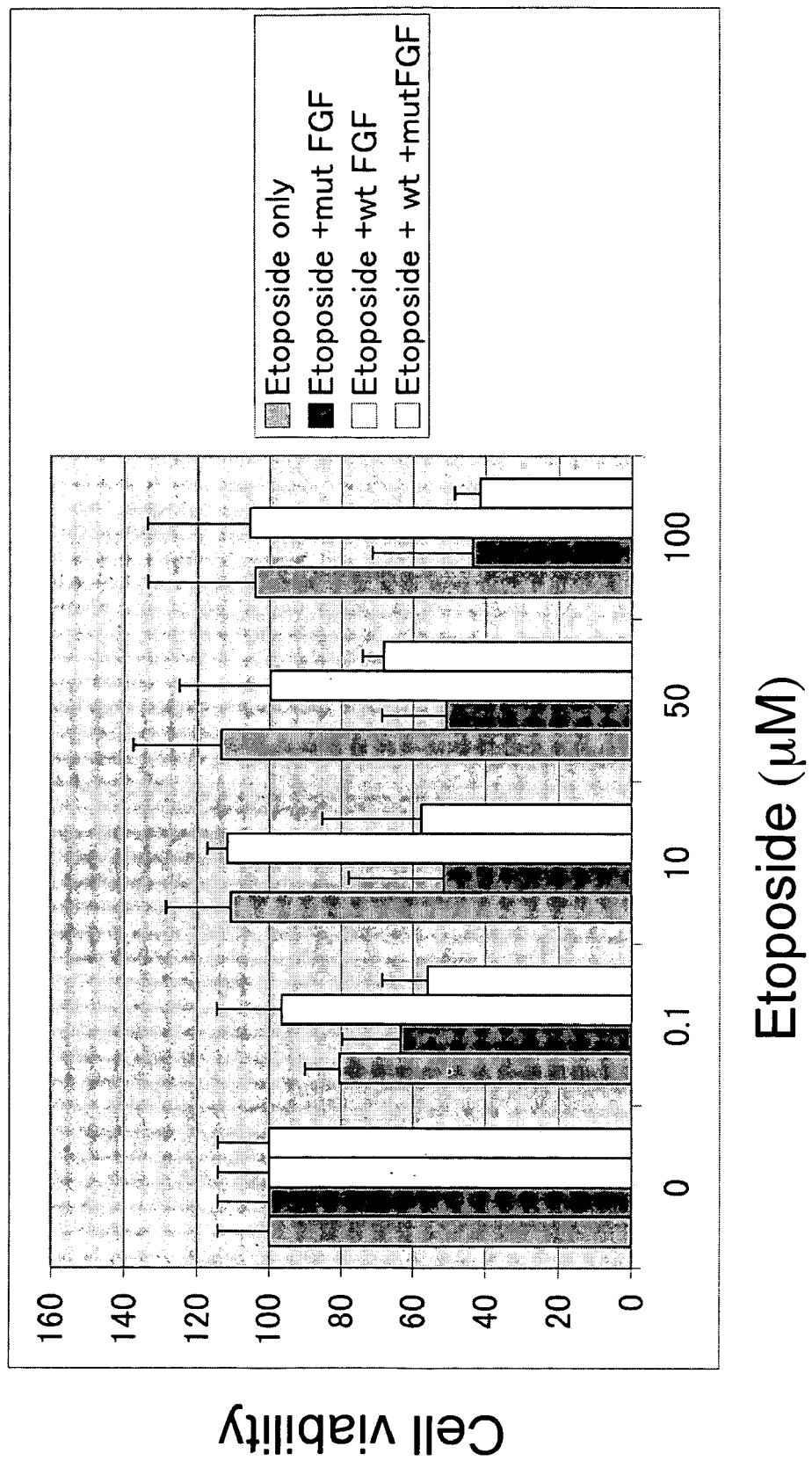

FIG. 10. Chemoresistance.

In FIG. 10, results are provided showing suppression of FGF-induced drug resistance in M21 melanoma cells. Resistance of melanoma cells was to etoposide-induced apoptosis. M21 human melanoma cells were cultured in DMEM with 1% FBS for 48 h, and then treated with etoposide (0.1-100 μM) in the presence or absence of wt or mutant FGF for 48 h, with cell viability determined.

Figure 11:
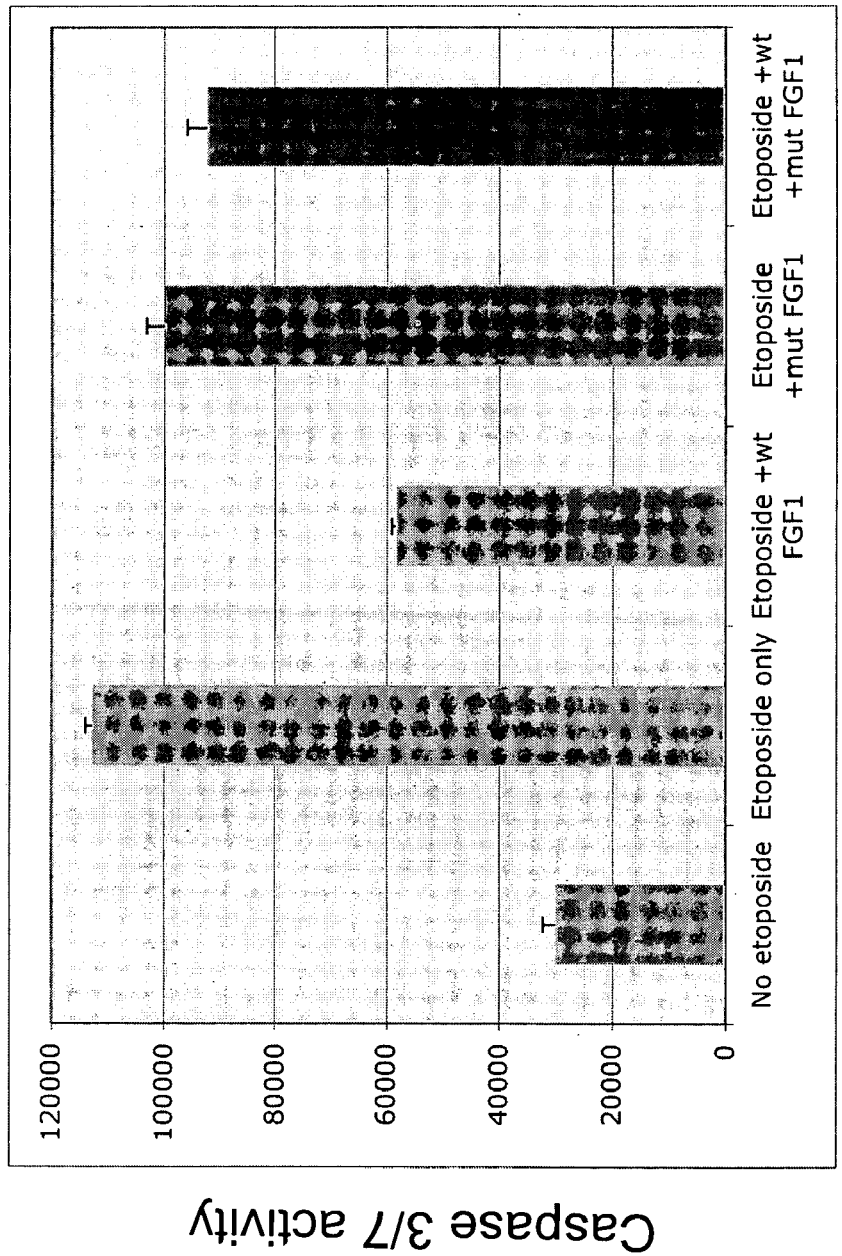

FIG. 11. Chemoresistance.

FIG. 11 shows the effect of the R50E FGF1 mutant on etooposide-induced caspase activation in M211 human melanoma cells.

Caspases 3/7 activity was determined to demonstrate resistance of melanoma cells to etoposide-induced apoptosis. M21 human melanoma cells were cultured in DMEM with 1% FBS for 48 h, and then treated with etoposide (0.1-100 μM) in the presence or absence of wt or mutant FGF for 48 h.

DETAILED DESCRIPTION OF THE INVENTION

Fibroblast growth factors (FGFs) are a family of heparin-binding growth factors and are critically involved in cell proliferation and migration. While integrins play a critical role in FGF signaling through "FGFR-integrin crosstalk," the molecular mechanism of the crosstalk is unclear. Immobilized FGF-1 binds to integrin $\alpha v\beta 3$ and $\alpha 5\beta 1$. The $\alpha v\beta 3$-binding site in FGF-1 is close to or overlaps with the heparin-binding site of FGF-1 but is distinct from that of FGFR. The $\alpha v\beta 3$ and heparin binding sites in FGF-1 are distinct since one mutation (R50E) blocked the binding to integrin but did not affect the binding to heparin. The FGF-1 mutants that do not bind to integrin were defective in inducing DNA synthesis, ERK1/2 activation, migration, and chemotaxis. These results show that direct binding of FGF-1 to integrins play a significant role in FGF-1 signaling, and that FGFR and integrins crosstalk on the cell surface through direct binding to FGF-1.

The results demonstrate how integrins interact with FGF-1, another pro-angiogenic FGF. It is shown that immobilized FGF-1 binds to integrin $\alpha v\beta 3$ and a5$\beta 1$. This interaction requires intact FGF-1 since heat treatment of FGF-1 blocked integrin binding. The $\alpha v\beta 3$-binding site of FGF-1 was localized by docking simulation and site-directed mutagenesis. The FGF-1 binding site is located close to or overlapping with the heparin-binding site of FGF-1. The $\alpha v\beta 3$ and heparin binding sites are distinct since one mutation (the R50E mutation) blocked integrin binding but not heparin binding. Mutations that block integrin binding did not block FGFR1 binding to FGF-1, and mutations that block binding to FGFR-1 did not affect integrin binding, suggesting that $\alpha v\beta 3$ and FGFR bind to FGF-1 in distinct manners.

The FGF-1 mutations that do not bind to integrins are defective in inducing DNA synthesis, ERK1/2 activation, migration, and chemotaxis of fibroblasts. These results show that the direct binding of FGF-1 to integrins plays a critical role in FGF-1 signaling, and that FGFR and integrins crosstalk on the cell surface through direct binding to FGF-1. FGF mutants, such as those described herein, are anti-FGF agents that may be used to block angiogenesis, cancer or tumor growth and excess wound healing.

Binding of Integkins to Immobilized FGF-1

Figure 1A:
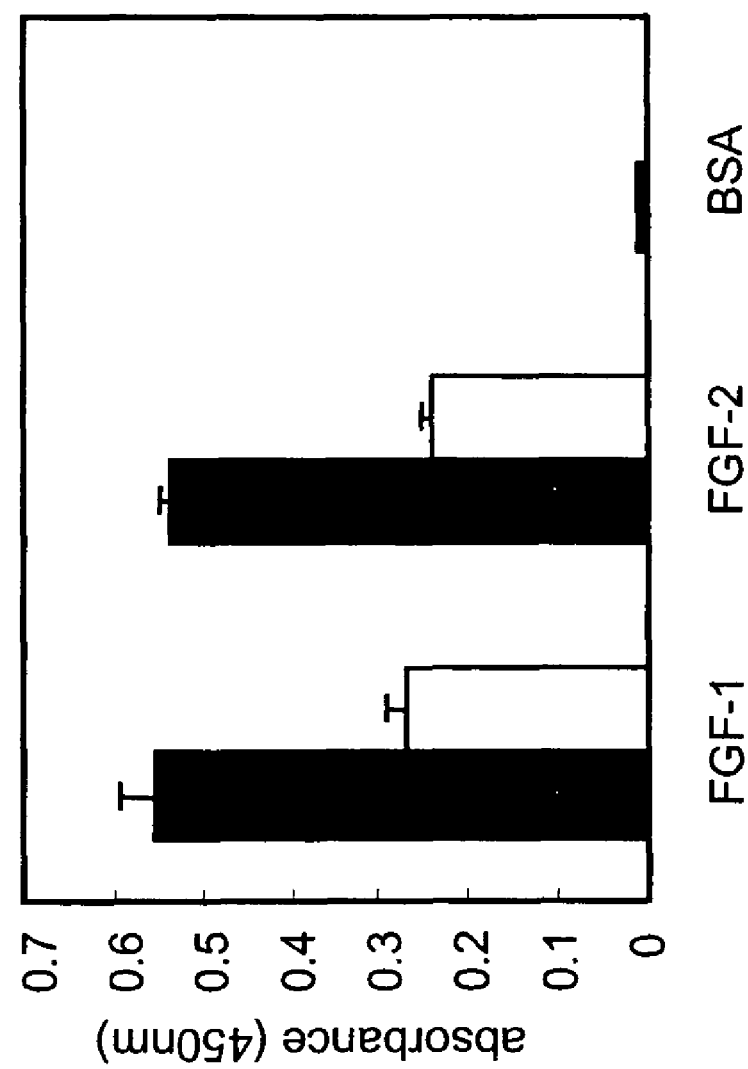
FIG. 1. Direct Binding of FGF-1 to Integrins
Figure 1B:
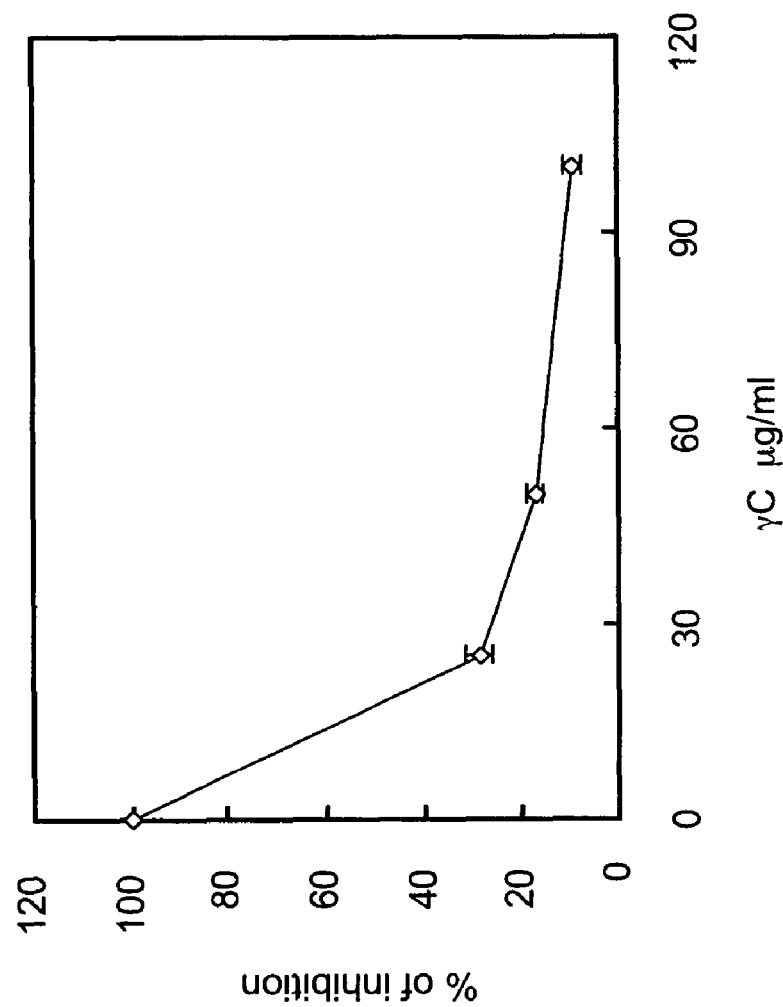

To identify the role of integrins in FGF signaling, a test was conducted as to whether FGF-1, another major FGF, interacts with integrins. To show integrin specific binding, recombinant soluble $\alpha v\beta 3$ was used for ELISA-type integrin binding assays. It was discovered that soluble $\alpha v\beta 3$ bound to immobilized FGF-1 and FGF-2 (as a positive control), but did not bind to BSA (FIG. 1A). MAb 7E3 blocked the binding of soluble $\alpha v\beta 3$ to FGF-1 and FGF-2, suggesting that binding to FGF-1 and FGF-2 is specific to $\alpha v\beta 3$. Whether FGF-1 binds to $\alpha v\beta 3$ in a manner similar to known integrin ligands was tested. A known ligand for $\alpha v\beta 3$, the fibrinogen $\gamma$ chain C-terminal domain ($\gamma$C) (Yokoyama et al., 2000; Yokoyama et al., 1999), was shown to effectively block FGF-1-$\alpha v\beta 3$ interaction (FIG. 1B), suggesting that FGF-1-binding site overlaps with that of $\gamma$C.

Figure 1C:
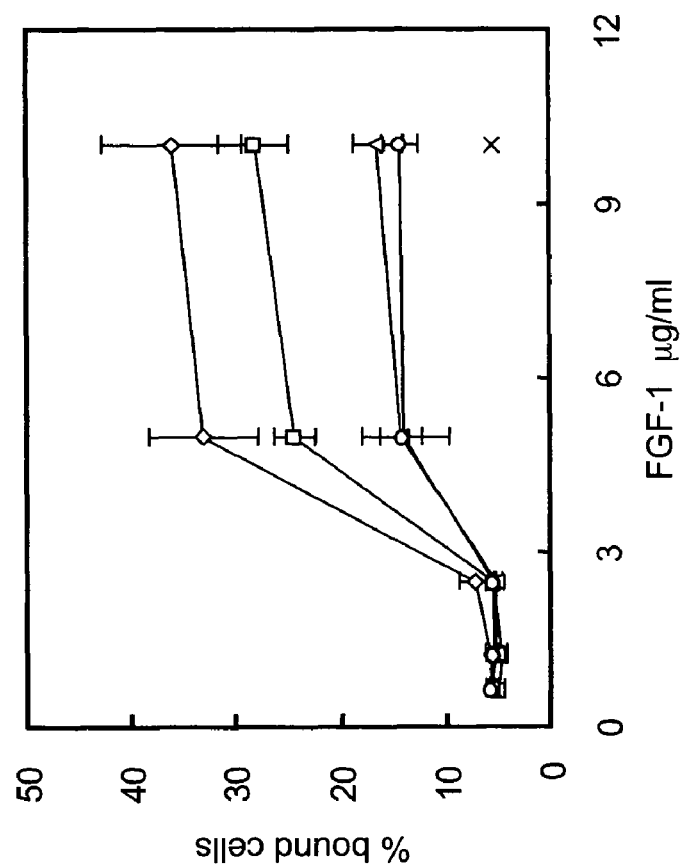
Figure 1D:
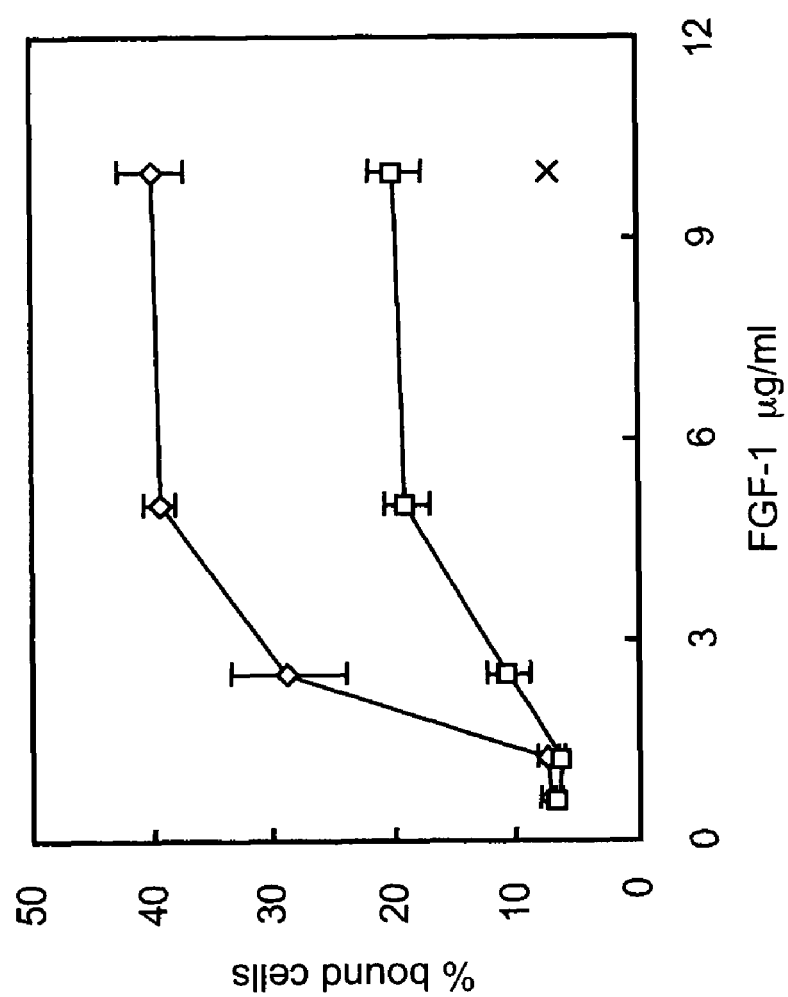

To test whether this integrin-FGF-1 interaction occurs in more biological systems, cell adhesion to immobilized FGF-1 was tested. It was found that both K562 erythroleukemia cells that over-express $\alpha v\beta 3$ (designated $\alpha v\beta 3$-K562 cells) and mock-transfected K562 cells bound to immobilized FGF!-1 in a dose-dependent manner in adhesion assays. K562 cells express endogenous $\alpha 5\beta 1$. The binding of $\alpha v\beta 3$-K562 cells to FGF-1 was suppressed by anti-$\alpha 5$ mAb (monoclonal antibody) KH72 and anti-$\beta 3$ mAb 7E3 and required both antibodies to effectively block adhesion to FGF-1 (FIG. 1C). The binding of K562 cells was suppressed by anti-$\alpha 5$ mAb KH72 (FIG. 1D). These results suggest that both $\alpha 5\beta 1$ and $\alpha v\beta 3$ bind to FGF-1 in this assay system.

Mapping Integrin-binding Sites in FGF-1 by Docking Simulation and Mutagenesis.

It has been reported that the binding of FGF-2 to integrins involves the DGR motifs in FGF-2 (Rusnati et al., 1997), but FGF-1 does not have the DGR motif or any known integrin-binding motifs. It has also been reported that $\alpha v\beta 3$ binds to heat-denatured FGF-2 (Rusnati et al., 1997), but it was discovered that soluble $\alpha v\beta 3$ did not bind to heat-denatured FGF-1 (FIG. 2A), indicating that the intact three-dimensional structure of FGF-1 is required for integrin binding.

To identify the mechanism of FGF-1 -integrin interaction, a docking simulation and site-directed mutagenesis was used. AutoDock is a set of docking tools widely used for predicting the conformation of small ligands bound to receptors (Goodsell and Olson, 1990; Morris et al., 1998; Morris et al., 1996), and the methods are being extended to predict protein-protein complex conformations (Saphire et al., 2001). Docking simulation of FGF-1-integrin $\alpha v\beta 3$ interaction was done using AutoDock. 50 dockings were performed, each one starting with a random initial position and orientation of FGF-1 (PDB code 1AXM) with respect to the integrin αvβ3. The results were clustered together by positional RMSD (root mean square distance) into families of similar conformations (FIG. 2B). Many of the docking conformations clustered well with the lowest docking energy −26.1 Kcal/mol (cluster 1), which is comparable to that of a known integrin ligand (fibrinogen γ chain C-terminal domain) (Yokoyama et al., 1999) (docking energy −24.3 Kcal/mol) in a similar docking simulation (data not shown).

These results predict that the docking conformation of cluster 1 (FIG. 2C) represents the most probable stable FGF-1 conformation upon binding to αvβ3. This model predicts that the integrin-binding interface of FGF-1 with integrin αvβ3 is distinct from the FGFR-binding site (Pellegrini et al., 2000), but is close to or overlapping with the heparin-binding site.

Several mutations were induced within the predicted interface of FGF-1 with integrin αvβ3 (Table 1), to identify critical residues for integrin binding. Mutant FGF-1 were generated in E. coli and purified as described in the methods section.

It was found that mutating 4 positively charged residues (Lys127/Lys128/Lys133/Arg134) simultaneously to Glu (designated the 4×E mutation) effectively blocked the binding of soluble αvβ3 to FGF-1 (FIG. 3A).

The Arg-50 to Glu (R50E) mutation also effectively blocked the binding of soluble αvβ3 to FGF-1.

Mutating three residues in the FGFR binding sites (the Glu102/Tyr109/Asn110 to Ala mutant, designated 3×A mutant), which are predicted from FGF1-FGFR2 complex structure (Pellegrini et al., 2000; Zhu et al., 1997) and mutagenesis data of FGF-2 (Zhu et al., 1997), did not affect integrin binding (FIG. 3A).

The 3×A mutation effectively blocked the binding of the FGFR1 fragment (domains 2 and 3, or D2D3), but the 4×E or R5OE mutation did not block the binding of the FGFR1 D2D3 fragment (FIG. 3B), showing that integrin-binding sites and FGFR1-binding sites are distinct.

A test was also conducted to see if these mutations can block heparin binding to FGF-1. It was found that the 4×E mutation completely blocked heparin binding but the R50E or 3×A mutation did not (FIG. 3C). These results show that the integrin-binding site overlaps with, but is not identical with, the heparin-binding site, and is distinct from the FGFR1-binding site (FIG. 3D). These results are consistent with the prediction by docking simulation.

Effects of FGF-1 Mutations that Block Integrin Binding on DNA Synthesis and Activation of ERK1/2

It has been well established that FGF-1 is a potent mitogen (reviewed in (Powers et al., 2000) and ERK1/2 plays an important role in transducing proliferative signals from receptor tyrosine kinases (Schlessinger, 2000). The mitogenic action of the FGFs is mediated in part by the activation of ERK1/2 (LaVallee et al., 1998; Pages et al., 1993).

The effect of the mutations that block integrin binding on FGF-1-induced DNA synthesis was tested in Balb 3T3 cells (FIG. 4). The FGF-1 induced BrdU incorporation was significantly blocked by the R50E and the 4×E mutations that block integrin binding. The negative control 3×A mutation that is defective in FGFR binding also blocked the BrdU incorporation. These results show that integrin binding to FGF-1 is critical for FGF-1-induced DNA synthesis besides the binding of FGF-1 to FGFR1.

The R50E mutant showed much less ability to induce ERK1/2 activation in Balb 3T3 cells than wild type FGF-1, and the 4×E mutation did not induce ERK1/2 activation at all (FIG. 6B), showing that the FGF-1 mutants have much reduced ability to activate ERK1/2. The negative control 3×A mutant defective in FGFR binding did not show ERK1/2 activation. These results show that integrin binding to FGF-1 besides FGFR binding are critical for FGF-1-induced DNA synthesis and ERK1/2 activation. Heparin did not enhance FGF-1-induced ERK1/2 activation or reverse the inhibitory effects of the FGF-1 mutations, showing that heparin is not a critical component for FGF-1 induced ERK1/2 activation in our assay system.

Effects of FGF-1 Mutations that Block Integrin Binding on Chemotaxis and Wound Healing It has been well established that FGF-1 is a potent inducer of cell migration and chemotaxis (Friesel and Maciag, 1995; Liu et al., 1999). The effect of mutations that block integrin binding on wound healing and chemotaxis was tested, and it was found that the R50E and 4×E mutants, as well as a negative control 3×A mutation, effectively blocked migration of Balb3T3 cells in scratch wound healing assays (FIG. 6A). The R50E and 4×E mutations blocked FGF-1-induced chemotaxis (FIG. 6B). The negative control 3×A mutant did not induce cell migration in scratch assays. Heparin was required for cell migration and chemotaxis assays. These results show that integrin binding to FGF-1 is critical for FGF-1's ability to induce cell migration and chemotaxis.

Binding of Integrins to FGF-1

The present study establishes that immobilized FGF-1 bound to integrins αvβ3 and α5β1 (and probably other integrins). While heat-denatured FGF-2 can bind to integrin αvβ3 (Rusnati et al., 1997) it was shown that FGF-1 requires the intact three-dimensional structure for integrin binding. Molecular docking simulation predicted the positions of amino acid residues critical for integrin binding and mutagenesis studies verified this prediction. The integrin binding site is distinct from the FGFR1-binding site, since mutations in the predicted integrin-binding site did not block FGFR1 binding, and mutations in the FGFR1-binding site did not affect integrin binding. The integrin-binding site of FGF-1 overlaps with the heparin-binding site. Since a point mutation (R50E) blocked integrin binding, but did not affect heparin binding, integrin-binding site and heparin-binding sites are not identical.

Critical Role of FGF-1-integrin Interaction in FGF-1 Signaling

The 4×E mutant strongly blocked FGF signaling, FGF-1 binding to heparin is mediated by a set of basic and polar residues that were identified in previous structural and mutagenesis experiments (DiGabriele et al., 1998; Fromm et al., 1997). The positively charged 4 residues in the 4×E mutant are engaged in heparin binding (DiGabriele et al., 1998; Fromm et al., 1997). Thus it is possible that this inhibition is due to loss of heparin binding, or integrin binding or both. The R50E mutant, which binds to heparin but not to integrin, is useful to study the specific role of integrin binding in FGF-1 signaling. The R50E mutant showed reduced ability to induce DNA synthesis, ERK1/2 activation, migration, and chemotaxis, suggesting that direct integrin binding to FGF-1 is critical for all aspects of FGF-1 signaling tested in this study. It has been reported that heparin potentiates FGF signaling, but the mechanism of this effect is unclear (Belford et al., 1992; Brown et al., 1995; Burgess et al., 1990; Kaplow et al., 1990; Thornton et al., 1983). The mutations (e.g., the R1 32E mutation) (Burgess et al., 1990) that block heparin binding to FGF-1 and reduce FGF-1 signaling appear to block integrin binding. This shows that the effects of these mutations may be due to inhibition of integrin binding besides inhibition of heparin binding. Interestingly, heparin did not enhance ERK1/2 activation induced by wild type FGF-1 or reverse the inhibitory effect of the R50E mutation in FGF-1 induced DNA synthesis and MAP kinase activation, showing that integrin binding, but not heparin binding, is required for DNA synthesis and ERK1/2 activation in our assay system. It is interesting that cell migration assays (wound healing and chemotaxis) required the presence of heparin in the present study, showing that FGF-1 induced cell proliferation and migration may use distinct signaling mechanisms.

Significance of FGF-1 as an Integrin Ligand

The present study provides a new insight into the role of integrins in FGF signaling. Current theory is that the binding of integrins to extracellular matrix (ECM) ligands is required for FGF signaling that leads to gene expression, cell proliferation, and migration (Comoglio et al., 2003; Eliceiri, 2001; Schwartz and Ginsberg, 2002). The present results show that FGF-1 itself acts as an integrin ligand during the FGF/FGFR/integrin crosstalk and direct binding to integrins is critical for FGF-1 to induce DNA synthesis, ERK1/2 activation, cell migration, and chemotaxis. The present study shows that integrins and FGFR1 can simultaneously bind to FGF-1, making a ternary complex during FGF-1 signaling.

It has been reported that the integrin-binding sites are cryptic in several known integrin ligands (e.g., fibrinogen and osteopontin) (Lishko et al., 2002). Immobilization and proteolytic cleavage are common mechanisms to uncover the cryptic integrin-binding sites. It has been reported that soluble FGF-2 does not bind to integrin, but immobilized FGF-2 does (Rusnati et al., 1997). Consistently, the binding of soluble FGF-1 to integrins could not be demonstrated. However, it is highly likely that soluble FGF-1 requires integrin binding to induce signal transduction, since the R50E mutation blocked signaling from soluble FGF-1. One possibility is that soluble FGF-1 or its mutants are immobilized on the cell surface and their integrin-binding sites are exposed. It is also possible that the binding of soluble FGF-1 to FGFR exposes the integrin-binding site in FGF-1.

This study predicts that integrins and FGFR directly interact with FGF (FIG. 7) instead of extracellular matrix ligands. Also, integrins and FGFR are co-localized in the focal contacts through direct binding to FGF-1, and many signaling molecules in the growth factor and integrin signaling pathways are recruited. Also integrin antagonists can block the FGF-integrin crosstalk and thereby block FGF signaling as in the current model. This is one of the mechanisms of the integrin FGF crosstalk. The FGF-1 mutants described herein may be used as anti-FGF agents (dominant negative mutants) that are useful in blocking angiogenesis, cancer or tumor growth, inflammation, excess wound healing, and resistance of tumor cells to chemotherapeutic agents (chemoresistance). Also, small molecules that bind to the integrin-binding sites of FGF can be used as antagonists to FGF signaling.

FRS2 Phosphorylation

Since MAP kinase activation and FAK phosphorylation can be mediated by either the integrin or the FGFR signaling pathway, FGF1 binding to either its FGFR or its integrin binding partner could have initiated the observed signal.

The binding of FGF to FGFR induces the dimerization of FGFR and the phosphorylation of several Tyr residues at the cytoplasmic domain of FGFR. Activation of FGFR results in tyrosine phosphorylation of the docking proteins Shc and FRS2α. FRS2α is a major intracellular substrate of the ligand-activated FGFR and is rapidly and highly tyrosine phosphorylated in cells upon FGF stimulation.

As seen in FIG. 8, wt FGF1 induced, but the R50E, 4×E, and 3×A mutations of FGF1 abolished, FGF 1-induced FRS2a phosphorylation. The results teach that the FGF1 mutations do not induce FGFR activation and subsequent phosphorylation of its downstream target FRS2α.

Similar results were obtained using Balb3T3 cells.

Tube Formation

As seen in reference to FIG. 9, the R50E mutant was shown to block tube formation by endothelial cells on matrigel in vitro in a dose-dependent manner while wt FGF1 enhanced it.

These results suggest that the R50E mutant has potential as antagonist for angiogenesis and resistance to chemotherapy. It has been reported that FGF1 binds to all known FGFR (FGFRs1 through 4), and thereby the R50E mutant may block the binding of other members of the FGF family.

Chemoresistance

It has been reported that FGF1 and 2 suppress apoptosis of cancer cells induced by chemotherapeutic agents (e.g., etoposide and doxorubicin). In Example 15, it was shown that the R50E mutant enhanced apoptosis induced by etoposide in M21-melanoma cells (FIG. 10). Also, the R50E mutant blocked inhibition of caspase activation by wt FGF (FIG. 11). Thus the R50E mutant worked as an FGF antagonist.

These results demonstrate that induced drug resistance in cancers or tumors can be diminished by the presence of competitive binding of mutant FGF, even in the presence of wt FGF.

EXAMPLES

Materials

The globular carboxyl-terminal domain of the fibrinogen γ-chain (γC) was synthesized in bacteria as an insoluble protein and refolded as previously described (Yokoyama et al., 1999). Recombinant soluble (αvβ3 was synthesized in CHO K1 cells using the soluble αv and β3 expression constructs provided by Tim Springer, (Center for Blood Research, Boston, Mass) and purified by Ni-NTA affinity chromatography as described (Takagi et al., 2001).

Example 1

Plasmid Construction, Protein Expression, and Purification of the Wild Type and Mutant FGF-1

The human FGF-1 and FGF-2 cDNAs were amplified using polymerase chain reaction (PCR) with human placenta library as a template. A Bgl II restriction site was introduced at the 5' end, an Eco RI site at the 3' end of the cDNA fragment with following primers: FGF-1, 5'-GCAGATCTTTTAATCT-GCCTCCAGGGAAT-3' [SEQ ID NO: 1] and 5'-GCGAAT-TCTTAATCAGAAGAGACTGGCAG-3'[SEQ ID NO: 2]. FGF-2: 5'-GCAGATCTCCCGCCTTGCCCGAGGATGGC-3' [SEQ ID NO: 3] and 5'-GCGAATTCTCAGCTCTTAG-CAGAAGACATTGG-3' [SEQ ID NO 4]. The resulting fragments were digested with Bgl II and Eco RI, and subcloned into the Bam HII/Eco RI sites of the pGEX-$^2$T (Amersham Pharmacia Biotech) vector.

Site-directed mutagenesis was performed using the Quick-Change method (Wang and Malcolm, 1999). The presence of the mutations was verified by DNA sequencing.

The wild type FGF-1 and its mutants were expressed in E. coli BL21 (DE3) and purified as described by the manufacturer's instructions (Pharmacia Biotech, Brussels, Belgium). After removing GST-tag by thrombin, wild type FGF-1, the R50E and the E101A/Y108A/N109A FGF-1 mutants were purified using a heparin Sepharose column (Amersham Pharmnacia Biotech). The K127E/K128E/K133E/R134E mutant was purified by gel filtration.

Example 2

Synthesis of the FGFR1 D2D3 Fragment.

A DNA fragment encoding amino acid residues 140 to 365 of the immunoglobulin-like domains D2 and D3 of FGFR was amplified by PCR with the full length human FGFR1 cDNA in the pcDNA3 (gift from Ann Hanneken, the Scripps Research Institute, La Jolla, Calif.) as a template. A Bam HI restriction site was introduced at the 5' end, Xho I site at the 3' end of the cDNA fragment with the following primers: 5'-GCGGATCCACAGATAACACCAAACCAAACC-3' [SEQ ID NO 5], 5'-GCCTCAGTCACCTCTCTTC-CAGGGCTTCC-3' [SEQ ID NO 6]. The resulting cDNA fragment was subcloned into the Bam HI/Xho I sites of the vector pET21a, and transformed into BL21 (DE3).

The protein was expressed as an insoluble protein, refolded as described (Plotnikov et al., 2000). The refolded protein was purified by affinity chromatography using the FGF-1 coupled to CNBr-activated Sepharose (Amersham Pharmacia Biotech) as an affinity matrix. FGF-1-Sepharose was incubated with crude refolded proteins 16 h at 4° C. After binding, the affinity matrix was washed with buffer containing 100 mM NaCl and 50 mM Tris (pH 7.4); and eluted with 1.2M NaCl, and 50 mM Tris (pH 7.4).

Example 3

Heparin Binding

Heparin Binding Assay

Wild type and mutant FGF-1 in 100 mM NaCl and 50 mM Tris/HCl (pH 7.4) were applied to heparin sepharose column (1 ml bed volume). The column was washed with same buffer, and bound proteins were eluted with a stepwise increase in NaCl concentration from 0.1 to 1.2 M. Fractions were analyzed by SDS-polyacrylamide gradient gel electrophoresis. Proteins were visualized by Coomassie Brilliant Blue staining.

Example 4

Docking Simulation

In the AUTODOCK 3.05 program, the ligand is presently compiled to a maximum size of 1024 atoms. The solvent-exposed $Mg^{2+}$ octahedral vertex was left empty in the model during docking calculations. Atomic solvation parameters and fractional volumes were assigned to the protein atoms by using the AddSol utility, and grid maps were calculated by using AutoGrid utility in AutoDock 3.05. A grid map with 127×127×127 points and a grid point spacing of 0.603 Angstrom included the whole MIDAS-containing face of the I-like domain of β3 and the β-propeller domain containing repeats 2-4, which are large enough to accommodate the FGF-1 structure. Kollman "united-atom" charges were used. AutoDock 3.05 uses a Lamarckian Genetic Algorithm (LGA) that couples a typical Darwinian genetic algorithm for global searching with the Solis and Wets algorithm for local searching. The LGA parameters were defined as follows: the initial population of random individuals had a size of 50 individuals; each docking was terminated with a maximum number of $1 \times 10^6$ energy evaluations or a maximum number of 27,000 generations, whichever came first; mutation and crossover rates were set at 0.02 and 0.80, respectively. An elitism value of 1 was applied, which ensured that the top ranked individual in the population always survived into the next generation. A maximum of 300 iterations per local search was used. The probability of performing a local search on an individual was 0.06, whereas the maximum number of consecutive successes or failures before doubling or halving the search step size was 4. This set of parameters was used for all dockings.

Example 5

Soluble Integrin Binding Assay

Binding assays were performed as previously described (Takagi et al., 2001). Native or heat-denatured FGF-1 in 0.1 M carbonate buffer, pH 9.4, were incubated in a polystyrene 96-well non-tissue culture plates surface overnight at 4° C. Unbound FGF-1 was removed, and 200 μl of 0.1 % bovine serum albumin in PBS was added and incubated for 60 min at room temperature. The wells were washed with PBS and soluble integrin αvβ3 in 50 μl in Hepes-Tyrode buffer supplemented with 1 mM $Mn^{2+}$ were added to the wells and incubated at room temperature for 60 min. After non-bound soluble integrin were removed by rinsing the wells with the same buffer. Horseradish peroxidase (HRP) conjugated anti His-tag mouse IgG was added to well and -incubated 60min. Non-bound antibodies were removed by rinsing the wells with the same buffer, bound integrins were quantified by measuring the absorbance of 450 nm developed from adding the substrate (3,3', 5,5'-tetramethylbenzidine) of HRP unbound protein was aspirated, and the wells were washed with PBS three times.

Example 6

Inhibition of FGF-1-αvβ3 Interaction by γC

FGF-1 (10 μg/ml) was immobilized to wells of 96-well plates. Soluble αvβ3 integrin was added to the wells with various concentration of γC. Bound integrin was detected by using HRP-conjugated anti-6His antibodies and its substrate as described above.

Example 7

Cell Adhesion Assay

Wells of polystyrene 96-well non-tissue culture plate were coated with wild type or mutants FGF-1 as above. In adhesion assay, cells ($10^5$ cells/well) in 100 μl of Hepes-Tyrode buffer supplemented with 1 mM $Mn^{2+}$ were added to the wells and incubated at 37° C. for 1 h. After non-bound cells were removed by rinsing the wells with the same buffer, bound cells were quantified by measuring endogenous phosphatase activity (Prater et al., 1991)

Example 8

DNA Synthesis

DNA synthesis was measured by BrdU incorporation. Balb 3T3 cells were plated on sterile cover slips in 6-well culture plates and serum starved in DMEM supplemented with 0.4% fetal calf serum for 48 h, and stimulated with 5 ng/ml wild type and mutant FGF-1 s for 24 h in the presence and absence of 5 μg/ml heparin. BrdU (10 μg/ml) was added to the medium for the last 6 h of the incubation. Cells were then fixed with 70% ethanol and incubated with 2N HCl. After the medium was neutralized with 0.1 M borate buffer (pH8.5), the cells were incubated with anti-BrdU antibody (BD PharMingen, San Diego, Calif.). BrdU incorporated cells were stained with HRP conjugated secondary antibody (Biorad) and metal enhanced diaminobenzidine substrate kit (Pierce, Rockford, Ill.). Diaminobenzidine positive and negative cells were counted from the digital images of three independent fields.

Example 9

MAP Kinase Activation

Balb3T3 cells were grown to confluence and serum starved in DMEM supplemented with 0.4% fetal calf serum for 24 h, and stimulated with wild type and mutant FGF-1 (5 ng/ml) in the presence or absence of 5 µg/ml heparin for 10 min at 37° C. Cells were washed twice with ice-cold PBS and lysed with the lysis buffer (20 mM Tris-HCI pH8.0, 120 mM NaCl, 5 mM EDTA, 0.5% Triton-X100, 1 mM PMSF, 1 mM DTT, 10 mM NaF, 1 mM $Na_3VO_4$, 10 µg/ml aprotinin). Cell lysates were separated on 4-12% NuPAGE Bis-Tris Gel (invitrogen). Proteins were then transferred to PVDF membranes (Millipore), probed with antibodies, and bound antibodies were detected by HRP-conjugated anti-mouse IgG and chemiluminescence HRP substrate (Pierce). The antibodies used were anti-phospho-ERK1/2, anti-ERKI/2 (Cell Signaling Technology).

Example 10

Wound Scratch Assay

Balb 3T3 cells were plated into 6-well cell culture plate. Cells were allowed to grow in DMEM containing 10% fetal calf serum for overnight, and then cells were washed with serum-free medium and starved for 24 h. A scratch was made across the cell layer using a pipette tip. After washing with serum-free medium twice, DMEM containing 10 ng/ml wild type or mutant FGF-1 together with 5 µg/ml heparin were added to cells. Plates were photographed at 0, 6, 12,and 24 h.

Example 11

Chemotaxis

A polycarbonate filter of 8 µm pore size of the Transwell insert was coated with 10 µg/ml of fibronectin (Sigma) overnight at 4° C. After washing, the insert was placed into a 24-well cell culture plate, and the lower portion of the plate was filled with 600 µl of serum-free DMEM containing 5 ng/ml wild type or mutant FGF-1. Balb 3T3 cells ($10^5$ cells/filter) were plated on filter and incubated 37° C. for 24 h, and cells were visualized by crystal violet staining (0.5% crystal violet in 50 mM Borate, pH 9.0, and 2% ethanol). The uncoated side of each filter was wiped with a cotton swab to remove cells that had not migrated through the filter. Migrated cells were counted from the digital images of stained cells. Determining the mean number of cells counted per field. Results are expressed as means±SD of the relative cell number with non- stimulated cells set as 100).

TABLE 1

Amino acid residues at the predicted interface between FGF-1 and integrin $\alpha v\beta 3$.

| FGF-1 | αv | β3 |
|---|---|---|
| Asn-33, Gly-34, Gly-35 | Met-118 | Tyr-122, Ser-123, Met-124 |
| His-36, Arg-39, Leu-41 | Ser-144, Gln-145, Asp-146 | Lys-125, Asp-126, Asp-127 |
| Asp-43, Thr-45, Val-46 | Ile-147, Asp-148, Ala-149 | Trp-129 |
| Asp-47, Gly-48, Thr-49 | Asp-150, Gly-151 | Tyr-166 |
| Arg-50, Asp-51, Arg-52 | Tyr-178 | |
| Ser-53, Asp-54 | | |
| Lys-127, Lys-128, Asn-129 | Thr-212, Gln-214, Ala-215 | Asp-179, Met-180, Lys-181 |
| Gly-130, Ser-131, Cys-132 | Ile-216, Asp-218, Asp-219 | Thr-182, Arg-214, Asn-215 |
| Lys-133, Arg-134, Arg-137 | Arg-248 | Arg-216, Ala-218, Asp-251 |
| Thr-138, Gly-141, Gln-142 | | Ala-252, Lys-253 |
| Lys-143, Ala-144 | | |

TABLE 2

Phenotype of FGF-1 mutants used in this study

| | αvβ3 binding | Heparin binding | FGFR binding | DNA synthesis | ERK½ activation | Wound healing | Chemotaxis |
|---|---|---|---|---|---|---|---|
| Wild type | Normal | Normal | Normal | Normal | Normal | Normal | Normal |
| R50E | Low | Normal | Normal | Low | Low | Low | Low |
| 4xE | Low | Low | Normal | Low | Low | Low | Low |
| 3xA | Normal | Normal | Low | Low | Low | Low | Low |

Example 12

A. FRS2 Phosphorylation

This experiment tested how the FGF1 mutations affect phosphorylation of FRS2α. It was found that wt FGF1 induced, but the R50E, 4×E, and 3×A mutations of FGF1 abolished, FGF1-induced FRS2a phosphorylation (FIG. 8). These results suggest that these FGF1 mutations do not induce FGFR activation and subsequent phosphorylation of its downstream target FRS2α.

Similar results were obtained with Balb3T3 cells.

Example 13

B. Tube Formation

Wells of 96-well FluoroNunc black plates were coated with 50 μl of matrigel basement membrane matrix (BD Bioscience) and allowed to gel at 37° C. for 30 min. Endothelial cells growing on the tissue culture plastic were trypsinized, washed, and added to the matrix-coated wells at 2×104 cells/well. Plating was performed in medium M-131 plus 0.1% hydrocortisone and 0.1 % FBS for Human microvascular endothelial (HMVE) cells. Cells were incubated for 24 h in the presence of wt or mutant FGF. To enhance images, calcein AM (Invitrogen) was added to the medium (10 tg/ml) and incubated for 15 min at 37oC. Digital images were taken by using a fluorescent microscope and analyzed by using ImageJ. (FIGS. 9A and 9B).

Example 15

C. Chemoresistance

Cells were plated on well of 96-well tissue culture plates and serum-starved for 48-72 h in DMEM supplemented with 0-1% FBS. Then cells were treated with etoposide (up to 100 μM) and wt or mutant FGF for additional 24-48 h. Cell viability was determined using CellTiter 96 MTS assay (Promega) and caspases 3/7 activity was determined by using Caspase-Glo 3/7 assay kit (Promega). FIGS. 10 and 11.

---

What is claimed is:

1. An isolated polypeptide comprising the amino acid sequence of SEQ ID NO:7, wherein the amino acid sequence of SEQ ID NO:7 has amino acid mutation R50E.

2. An isolated polypeptide comprising the amino acid sequence of SEQ ID NO:7, wherein the amino acid sequence of SEQ ID NO:7 has amino acid mutations E101A, Y109A, and N110A.

3. An isolated polypeptide comprising the amino acid sequence of SEQ ID NO:7, wherein the amino acid sequence of SEQ ID NO:7 has amino acid mutations K127E, K128E, K133E, and R134E.

4. An isolated polypeptide comprising the amino acid sequence of SEQ ID NO:7, wherein the amino acid sequence of SEQ ID NO:7 has amino acid mutation N33A.

5. An isolated polypeptide comprising the amino acid sequence of SEQ ID NO:7, wherein the amino acid sequence of SEQ ID NO:7 has amino acid mutation R50Q.

6. An isolated polypeptide comprising the amino acid sequence of SEQ ID NO:7, wherein the amino acid sequence of SEQ ID NO:7 has a mutation in the region Arg-50, Asp-51, Arg-52.

7. An isolated polypeptide comprising the amino acid sequence of SEQ ID NO:7, wherein the amino acid sequence of SEQ ID NO:7 has amino acid mutations K127Q and K128Q.

8. An isolated polypeptide comprising the amino acid sequence of SEQ ID NO:7, wherein the amino acid sequence of SEQ ID NO:7 has amino acid mutations K133Q and R134Q.

9. A pharmaceutical composition comprising the polypeptide of any one of claims 1-8 and a carrier.

* * * * *